United States Patent [19]
Syoji et al.

[11] Patent Number: 5,393,890
[45] Date of Patent: Feb. 28, 1995

[54] PIPERIDINE DERIVATIVES AND HYPOTENSIVES CONTAINING THE SAME

[75] Inventors: Masataka Syoji; Kozo Toyota; Chikahiko Eguchi; Ryoto Yoshimoto; Yoshikatsu Koyama; Hideki Domoto; Akira Kamimura, all of Kawasaki, Japan

[73] Assignee: Ajinomoto Co., Inc., Tokyo, Japan

[21] Appl. No.: 269,628

[22] Filed: Jul. 1, 1994

Related U.S. Application Data

[63] Continuation of Ser. No. 72,458, Jun. 7, 1993, abandoned, which is a continuation of Ser. No. 655,775, Feb. 15, 1991, Pat. No. 5,250,681, which is a continuation of Ser. No. 443,438, Nov. 30, 1989, abandoned, which is a continuation of Ser. No. 354,880, May 22, 1989, Pat. No. 5,231,105, which is a continuation of Ser. No. 201,911, Jun. 2, 1988, abandoned.

[30] Foreign Application Priority Data

Nov. 30, 1988 [JP] Japan .................. 63-303461
Mar. 16, 1989 [JP] Japan .................... 1-60459

[51] Int. Cl.$^6$ ............... C07D 491/052; C07D 513/04; C07D 405/04; C07D 409/04
[52] U.S. Cl. ............................ 546/80; 546/89; 546/187; 546/191; 546/196; 546/202; 546/203; 546/204; 546/208; 546/209; 546/210; 546/213; 546/214
[58] Field of Search ............ 546/80, 89, 187, 191, 546/196, 202, 203, 204, 208, 209, 210, 213, 214

[56] References Cited

U.S. PATENT DOCUMENTS

| | | | |
|---|---|---|---|
| 4,031,222 | 6/1977 | Remy | 424/267 |
| 4,073,912 | 2/1978 | Kaiser et al. | 424/267 |
| 4,356,184 | 10/1982 | Deason et al. | 546/202 X |
| 4,912,222 | 3/1990 | Griffith et al. | 546/203 |
| 5,231,105 | 1/1993 | Shoji et al. | 514/325 |

FOREIGN PATENT DOCUMENTS

| | | |
|---|---|---|
| 005607 | 11/1979 | European Pat. Off. |
| 1153977 | 6/1969 | United Kingdom |

*Primary Examiner*—Richard L. Raymond
*Attorney, Agent, or Firm*—Oblon, Spivak, McClelland, Maier & Neustadt

[57] ABSTRACT

A piperidine compound of the formula (I):

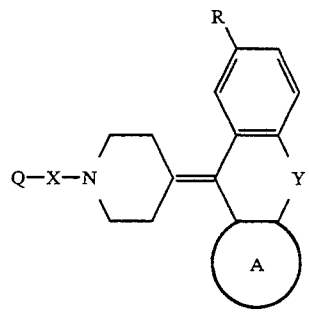

wherein A is a fused aromatic ring; R is hydrogen, chloro or methoxy; X is $(CH_2)_n$, which may be substituted, in which n is 0 or an integer of 1 to 10, —CH=CH—, —C≡C—, —O—, —S—, —NH—, —N(COCH$_3$)—, —N(COOC$_2$H$_5$)—, —N(CHO)—, —N(CH$_3$)—, —CO—, —SO—, or —SO$_2$—; Y is —CH=CH—, —CH$_2$CH$_2$—, —CH$_2$CO—, —O—, —S—, —NH—, —OCH$_2$—, —SCH$_2$—, —NHCH$_2$—, —CH(OH)CH$_2$— or —CH(OH)CH(OH)—; and Q is substituted or unsubstituted n-hexyl, carboxypropyl, ethoxycarbonylpropyl, cyanopropyl, cyclohexyl, phenyl, indanyl, naphthyl, tetrahydronaphthyl, benzocycloheptyl, piperidinyl, tetrahydroisoquinolinyl, indolyl, pyrolyl, furyl, thienyl, thiazolyl, oxazolyl or N-methylpyrolyl, wherein any one or more of the —(CH$_2$)-groups of the hexyl, carboxypropyl, ethoxycarbonylpropyl and cyanopropyl groups may be replaced by —CH=CH—, —C≡C—, —O—, —S—, —NH—, —N(COCH$_3$), —N(COC$_2$H$_5$)—, —N(CHO)—, —N(CH$_3$), —CO—, —SO— or —SO$_2$—, and wherein one or more of the —(CH$_2$)-groups in X and Q may be substituted by —(CH$_2$)$_4$— or —(CH$_2$)$_5$— thereby forming a ring structure.

12 Claims, No Drawings

PIPERIDINE DERIVATIVES AND HYPOTENSIVES CONTAINING THE SAME

This application is a continuation of application Ser. No. 08/072,458, filed Jun. 7, 1993, now abandoned, which is a continuation of application Ser. No. 07/655,775, filed Feb. 15, 1991, now U.S. Pat. No. 5,250,681, which is a continuation of application Ser. No. 07/443,438, filed Nov. 30, 1989, now abandoned, which is a continuation of application Ser. No. 07/354,880, filed May 22, 1989, now U.S. Pat. No. 5,231,105, which is a continuation of application Ser. No. 07/201,911, filed Jun. 2, 1988, now abandoned.

BACKGROUND OF THE INVENTION

FIELD OF THE INVENTION

The present invention relates to a piperidine derivative and hypotensives containing the same.

DESCRIPTION OF THE BACKGROUND

It is said that there are about 13,000,000 patients with hypertension in Japan and its frequency of occurrence in individuals becomes greater with advancing age. Further, as the age of a given population increases, increased attention is directed to hypertension which becomes more and more of a dangerous factor in severe heart and cerebral diseases represented by cardiac infarction and cerebral apoplexy. In recent years, calcium antagonists or angiotensin convertase inhibitors have been widely used as excellent primary selection drugs for treatment of hypertension. But the pharmaceutical effects or safety of these hypotensives have recently come into question.

A need therefore continues to exist for new hypotensive agents which exhibit excellent pharmaceutical effects and safety which can be industrially prepared at low cost and in a simple manner.

SUMMARY OF THE INVENTION

Accordingly, one object of the present invention is to provide an effective hypotensive agent which is relatively simple to prepare at low cost.

Briefly, this object and other objects of the present invention as hereinafter will become more readily apparent can be attained by a piperidine derivative of formula (I):

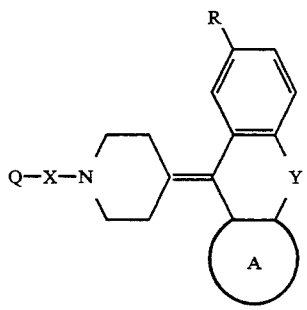

(I)

wherein A is a fused aromatic ring; R is hydrogen, chloro or methoxy; X is $(CH_2)_n$, which may be substituted, in which n is 0 or an integer of 1 to 10, —CH═CH—, —C≡C—, —O—, —S—, —NH—, —N(COCH$_3$)—, —N(COOC$_2$H$_5$)—, —N(CHO)—, —N(CH$_3$)—, —CO—, —SO—, or —SO$_2$—; Y is —CH═CH—, —CH$_2$CH$_2$—, —CH$_2$CO—, —O—, —S—, —NH—, —OCH$_2$—, —SCH$_2$—, —NHCH$_2$—, —CH(OH)CH$_2$—or —CH(OH)CH(OH)—; and Q is substituted or unsubstituted n-hexyl, carboxypropyl, ethoxycarbonylpropyl, cyanopropyl, cyclohexyl, phenyl, indanyl, naphthyl, tetrahydronaphthyl, benzocycloheptyl, piperidinyl, tetrahydroisoquinolinyl, indolyl, pyrolyl, furyl, thienyl, thiazolyl, oxazolyl or N-methylpyrolyl, wherein any one or more of the —(CH$_2$)-groups of the hexyl, carboxypropyl, ethoxycarbonylpropyl and cyanopropyl groups may be replaced by —CH═CH—, —C≡C—, —O—, —S—, —NH—, —N(COCH$_3$), —N(COC$_2$H$_5$)—, —N(CHO)—, —N(CH$_3$)—, —CO—, —SO— or —SO$_2$—, and wherein one or more of the —(CH$_2$)-groups in X and Q may be substituted by —(CH$_2$)$_4$— or —(CH$_2$)$_5$— thereby forming a ring structure.

DETAILED DESCRIPTION OF THE PREFERRED EMBODIMENTS

It has now been discovered that piperidine derivatives of the formula (I) above are effective as hypotensive agents. The present piperidine derivative exhibits excellent hypotensive action, its method of synthesis is simple and its derivatives can be easily prepared.

In formula (I), the fused aromatic ring (A) is a fused benzene, thiophene, pyridine or the like ring. Further, in formula (I) above, substituents X and Q may be substituted by at least one substituent selected from the group consisting of H(CH2)n, wherein n is 1 to 10, C$_1$(CH$_2$)$_3$, allyl, phenyl, isopropyl, hydroxy, methoxy, ethoxy, fluoro, chloro, acetoxy, 2-methoxyacetoxy, ethoxycarboxy, carboxyl, methoxycarbonyl, ethoxycarbonyl, cyano, imidazolylmethyl, trifluoromethyl, benzoyl, 2-hydroxybenzyl, nitro, amino, acetylamino, propanoylamino, butanoylamino, pivaloylamino, trifluoromethylamino, methoxycarbonylamino, ethoxycarbonylamino, cinnamoylamino, methanesulfonylamino, N,N-bis(methanesulfonyl)amino, aminocarbonyl, aminosulfonyl, hydroxymethyl and acetoxymethyl.

The method of administration of the present piperidine derivative when used as a hypotensive, include oral and parenteral routes. Dose is determined depending upon age, body weight and condition of the patient and route of administration. Daily dose is generally 0.01 to 2000 mg/kg for oral administration. In the case of parenteral administration, the daily dose is 0.01 to 1000 mg/kg. The present piperidine derivative may be prepared in the form of ordinary preparations such as for example, tablets, powders, capsules, solutions, sugar-coated tablets or depots, which may be prepared in a conventional manner using conventional preparation aids. For example, tablets can be obtained by mixing the piperidine derivative of the present invention diluents (e.g., lactose, calcium carbonate or calcium phosphate), binders (e.g., gum arabic, corn starch or gelatin), swelling agents (e.g., alginic acid, corn starch or pregelinated starch), sweeteners (e.g., sucrose or saccharin), flavors (e.g., peppermint, Gaultheria adenothrix oil or cherry), lubricating and wetting agents (e.g., magnesium stearate, talc or carboxymethyl cellulose).

Having now generally described this invention, a further understanding can be obtained by reference to certain specific examples which are provided herein for purposes of illustration only and are not intended to be limited unless otherwise specified.

Unless otherwise indicated, the developing conditions for silica gel TLC procedures were under chloroform/methanol=9/1. Mass spectra (MS) were performed in the FD mode (m/z) and nuclear magnetic resonance spectra (NMR) were measured using tetramethylsilane as the internal standard and CDCl$_3$ as the solvent.

EXAMPLE 1

4-(5H-Dibenzo[a,d]cyclohepten-5-ylidene)-1-hexylpiperidine hydrochloride

A solution of 273 mg (1 mmol) of 4-(5H-dibenzo[a,d]cyclohepten-5-ylidene)-1-hexylpiperidine, 165 mg (1 mmol) of 1-bromohexane, 745 mg (5 mmols) of sodium iodide and 414 mg (3 mmols) of potassium carbonate in 20 ml of methyl isobutyl ketone was stirred and refluxed at 120° C. overnight on an oil bath. After the reaction, the mixture was washed by adding 20 ml of water thereto. Then the organic phase was separated and the solvent was distilled off under reduced pressure. After purifying by silica gel column chromatography (eluent: methanol/chloroform, 1/100–1/50), the product was converted into the hydrochloride with an equimolar hydrogen chloride/dioxane solution.

Amount yielded 180 mg
Yield 46%
TLC Rf=0.68
MS 357 (M+)
NMR 0.83 (3H, t), 1.2–1.4 (6H, m), 1.7–1.9 (2H, m), 2.31 (2H, dd), 2.53 (2H, d), 2.7–2.8 (2H, m), 3.14 (2H, dd), 3.38 (2H, dd), 3.38 (2H, d), 6.92 (2H, s), 7.2–7.4 (8H, m)

Hereafter procedures were carried out in manner similar to Example 1.

EXAMPLE 2

4-(5H-Dibenzo[a,d]cyclohepten-5-ylidene)-1-octylpiperidine hydrochloride

Amount yielded 300 mg
Yield 72%
TLC Rf=0.71
MS 385 (M+)
NMR 0.85 (3H, t), 1.2–1.4 (10H, m), 1.7–2.0 (2H, m), 2.30 (2H, dd), 2.53 (2H, d), 2.7–2.9 (2H, m), 3.13 (2H, dd), 3.38 (2H, d), 6.90 (2H, s), 7.1–7.4 (8H, m)

EXAMPLE 3

1-Decyl-4-(5H-dibenzo[a,d]cyclohepten-5-ylidene)-piperidine hydrochloride

Amount yielded 300 mg
Yield 67%
TLC Rf=0.75
MS 413 (M+)
NMR 0.85 (3H, t), 1.2–1.4 (14H, m), 1.7–1.9 (2H, m), 2.33 (2H, dd), 2.54 (2H, d), 2.7–2.8 (2H, m), 3.15 (2H, dd), 3.39 (2H, d), 6.92 (2H, s), 7.1–7.4 (8H, m)

EXAMPLE 4

4-(5H-Dibenzo[a,d]cyclohepten-5-ylidene)-1-dodecylpiperidine hydrochloride

Amount yielded 1.10 g
Yield 92%
TLC Rf=0.78
MS 441 (M+)
NMR 0.85 (3H, t), 1.1–1.5 (18H, m), 1.7–1.9 (2H, m), 2.32 (2H, dd), 2.54 (2H, d), 2.7–2.8 (2H, m), 3.12 (2H, dd), 3.36 (2H, d), 6.93 (2H, s), 7.1–7.4 (8H, m)

EXAMPLE 5

4-(5H-Dibenzo[a,d]cyclohepten-5-ylidene)-1-tetradecylpiperidine hydrochloride

Amount yielded 1.20 g
Yield 95%
TLC Rf=0.78
MS 469 (M+)
NMR 0.82 (3H, t), 1.1–1.5 (22H, m), 1.7–1.9 (2H, m), 2.33 (2H, dd), 2.55 (2H, d), 2.7–2.8 (2H, m), 3.15 (2H, dd), 3.40 (2H, d), 6.92 (2H, s), 7.1–7.4 (8H, m)

EXAMPLE 6

4-(5H-Dibenzo[a,d]cyclohepten-5-ylidene)-1-hexadecylpiperidine hydrochloride

Amount yielded 1.18 g
Yield 88%
TLC Rf=0.80
MS 497 (M+)
NMR 0.80 (3H, t), 1.1–1.6 (26H, m), 1.7–1.9 (2H, m), 2.33 (2H, dd), 2.58 (2H, d), 2.7–2.8 (2H, m), 3.20 (2H, dd), 3.40 (.2H, d), 6.88 (2H, s), 7.1–7.4 (8H, m)

EXAMPLE 7

1-Cyclohexylmethyl-4-(5H-dibenzo[a,d]cyclohepten-5-ylidene)piperidine hydrochloride Amount yielded 520 mg
Yield 51%
TLC Rf=0.75
MS 369 (M+)
NMR 0.8–2.1 (11H, m), 2.42 (2H, dd), 2.65 (2H, d), 2.78 (2H, d) , 3.20 (2H, dd), 3.42 (2H, d), 6.91 (2H, s), 7.1–7.4 (8H, m)

EXAMPLE 8

1-Cyclohexyl-2-(4-(5H-dibenzo[a,d]cyclohepten-5-ylidene)-1-piperidinyl)ethane hydrochloride Amount yielded 780 mg
Yield 74%
TLC Rf=0.75
MS 383 (M+)
NMR 0.8–2.1 (13H, m), 2.45 (2H, dd) , 2.67 (2H, d), 2.7–2.9 (2H, m), 3.0 (2H, dd) , 3.48 (2H, d) , 6.94 (2H, s), 7.1–7.4 (8H, m)

EXAMPLE 9

1-Cyclohexyl-3-(4-(5H-dibenzo[a,d]cyclohepten-5-ylidene)-1-piperidinyl)propane hydrochloride Amount yielded 1.02 g
Yield 94%
TLC Rf=0.77
MS 397 (M+)
NMR 0.8–2.1 (15H, m) , 2.47 (2H, dd), 2.68 (2H, d), 2.7–2.9 (2H, m), 3.0 (2H, dd), 3.49 (2H, d), 6.94 (2H, s), 7.1–7.4 (8H, m)

EXAMPLE 10

1-Cyclohexyl-4-(4-(5H-dibenzo[a,d]cyclohepten-5-ylidene)-1-piperidinyl)butane hydrochloride Amount yielded 815 mg
Yield 72%
TLC Rf=0.78

MS 411 (M+)
NMR 0.8–2.1 (17H, m), 2.28 (2H, dd), 2.52 (2H, 2.7–2.9 (2H, m), 3.08 (2H, dd), 3.35 (2H, d), 6.92 (2H, s), 7.1–7.4 (8H, m)

EXAMPLE 11

1-Cyclohexyl-5-(4-(5H-dibenzo[a,d]cyclohepten-5-ylidene)-1-piperidinyl)pentane hydrochloride Amount yielded 750 mg
Yield 65%
TLC Rf=0.80
MS 411 (M+)
NMR 0.8–2.1 (19H, m), 2.25 (2H, dd), 2.68 (2H, d), 2.7–2.9 (2H, m), 3.12 (2H, dd), 3.38 (2H, d), 6.92 (2H, s), 7.1–7.4 (8H, m)

EXAMPLE 12

1-Benzyl-4-(5H-dibenzo[a,d]cyclohepten-5-ylidene)-piperidine hydrochloride

Amount yielded 320 mg
Yield 80%
TLC Rf=0.42
MS 363 (M+)
NMR 2.28 (2H, dd), 2.52 (2H, d), 3.14 (2H, dd), 3.31 (2H, d), 4.01 (2H, d), 6.90 (2H, s), 7.1–7.6 (13H, m)

EXAMPLE 13

2-(4-(5H-Dibenzo[a,d]cyclohepten-5-ylidene)-1-piperidinyl)-1-phenylethane hydrochloride Amount yielded 310 mg
Yield 75%
TLC Rf=0.45
MS 377 (M+)
NMR 2.28 (2H, dd), 2.51 (2H, d), 3.0–3.3 (6H, m), 3.47 (2H, d), 6.90 (2H, s), 7.1–7.4 (13H, m)

EXAMPLE 14

3-(4-(5H-Dibenzo[a,d]cyclohepten-5-ylidene)-1-piperidinyl)-1-phenylpropane hydrochloride Amount yielded 330 mg
Yield 77%
TLC Rf=0.50
MS 391 (M+)
NMR 2.1–2.4 (4H, m), 2.51 (2H, d), 2.65 (2H, t), 2.7–2.9 (2H, m), 3.12 (2H, dd), 3.38 (2H, d), 6.90 (2H, s), 7.1–7.4 (13H, m)

EXAMPLE 15

4-(4-(5H-Dibenzo[a,d]cyclohepten-5-ylidene)-1-piperidinyl)-1-phenylbutane hydrochloride Amount yielded 180 mg
Yield 41%
TLC Rf=0.50
MS 405 (M+)
NMR 1.4–1.9 (4H, m), 2.28 (2H, dd), 2.52 (2H, d), 2.61 (2H, t), 2.7–2.8 (2H, m), 3.12 (2H, .dd), 3.35 (2H, d), 6.90 (2H, s), 7.1–7.4 (13H, m)

EXAMPLE 16

5-(4-(5H-Dibenzo[a,d]cyclohepten-5-ylidene)-1-piperidinyl)-1-phenylpentane hydrochloride Amount yielded 110 mg
Yield 24%,
TLC Rf=0.55
MS 419 (M+)
NMR 1.2–1.9 (6H, m), 2.25 (2H, dd), 2.52 (2H, d), 2.60 (2H, t), 2.7–2.8 (2H, m), 3.08 (2H, dd), 3.35 (2H, d), 6.90 (2H, s), 7.1–7.4 (13H, m)

EXAMPLE 17

6-(4-(5H-Dibenzo[a,d]cyclohepten-5-ylidene)-1-piperidinyl)-1-phenylhexane hydrochloride Amount yielded 315 mg
Yield 67%
TLC Rf=0.56
MS 433 (M+)
NMR 1.1–1.9 (8H, m), 2.26 (2H, dd), 2.56 (2H, d), 2.61 (2H, t), 2.7–2.8 (2H, m), 3.10 (2H, dd), 3.35 (2H, d), 6.91 (2H, s), 7.1–7.4 (13H, m)

EXAMPLE 18

7-(4-(5H-Dibenzo[a,d]cyctohepten-5-ylidene)-1-piperidinyl)-1-phenylheptane hydrochloride Amount yielded 267 mg
Yield 55%
TLC Rf=0.56
MS 447 (M+)
NMR 1.1–1 (10H, m), 2.25 (2H, dd), 2.55 (2H, d), 2.65 (2H, t), 2.7–2.8 (2H, m), 3.07 (2H, dd), 3.32 (2H, d), 6.90 (2H, s), 7.1–7.4 (13H, m)

EXAMPLE 19

2-(4-(5H-Dibenzo[a,d]cyclohepten-5-ylidene)-1-piperidinyl)-1-phenoxyethane hydrochloride Amount yielded 1.95 g
Yield 55%
TLC Rf=0.56
MS 393 (M+)
NMR (fee base) 2.1–2.5 (2H, m), 2.58 (2H, t), 2.6–2.7 (2H, m), 4.05 (2H, t), 6.89 (2H, d), 6.92 (2H, s), 7.1–7.4 (11H, m)

EXAMPLE 20

3-(4-(5H-Dibenzo[a,d]cyclohepten-5-ylidene)-1-piperidinyl)-1-phenoxypropane hydrochloride Amount yielded 2.15 g
Yield 48%
TLC Rf=0.58
MS 407 (M+)
NMR (free base) 1.97 (2H, tt), 2.1–2.5 (6H, m), 2.54 (2H, t), 2.6–2.7 (2H, m), 3.97 (2H, dd), 6.86 (2H, d), 6.90 (2H, s), 7.1–7.4 (11H, m)

EXAMPLE 21

4-(4-(5H-Dibenzo[a,d]cyclohepten-5-ylidene)-1-piperidinyl)-1-phenoxybutane hydrochloride Amount yielded 1.18 g
Yield 86%
TLC Rf=0.61
MS 421 (M+)
NMR (free base) 1.8–2.7 (14H, m), 3.96 (2H, t), 6.87 (2H, d), 6.90 (2H, s), 7.1–7.4 (11H, m)

EXAMPLE 22

2-(4-(5H-dibenzo[a,d]cyclohepten-5-ylidene)-1-piperidinyl)-1-phenylthioethane hydrochloride Amount yielded 0.97 g
Yield 87%
TLC Rf=0.55
MS 409 (M+)

NMR (free base) 2.0–2.6 (10H, m), 2.78 (2H, t), 6.86 (2H, s), 7.1–7.4 (11H, m)

EXAMPLE 23

3-(4-(5H-Dibenzo[a,d]cyclohepten-5-ylidene)-1-piperidinyl)-1-phenylthiopropane hydrochloride Amount yielded 0.85 g
Yield 74%
TLC Rf=0.62
MS 423 (M+)
NMR (free base) 1.73 (2H, tt), 2.0–2.6 (10H, m), 2.80 (2H, t), 6.88 (2H, d), 7.1–7.4 (11H, m)

EXAMPLE 24

4-(4-(5H-Dibenzo[a,d]cyclohepten-5-ylidene)-1-piperidinyl)-1-phenylthiobutane hydrochloride Amount yielded 0.85 g
Yield 72%
TLC Rf=0.62
MS 437 (M+)
NMR (free base) 1.6–2.6 (14H, m), 2.80 (2H, t), 6.88 (2H, d), 7.1–7.4 (11H, m)

EXAMPLE 25

4-(5H-Dibenzo[a,d]cyclohepten-5-ylidene)-1-(2-(2-nitrobenzenesulfonyl)aminoethyl)piperidine hydrochloride TLC Rf=0.72
MS 502 (M+)

EXAMPLE 26

1-(2-(2-Aminobenzenesulfonyl)aminoethyl)-4-(5H-dibenzo[a,d]-cyclohepten-5-ylidene)piperidine hydrochloride TLC Rf=0.51
MS 472 (M+)

EXAMPLE 27

4-(5H-Dibenzo[a,d]cyclohepten-5-ylidene)-1-(2-(2-ethoxycarbonylbenzenesulfon6yl)aminoethyl)piperidine hydrochloride TLC Rf=0.68
MS 544 (M+)

EXAMPLE 28

3-(2-((4-(5H-Dibenzo[a,d]cyclohepten-5-ylidene)-1-piperidinyl)ethyl)-2,4(1H,3H)quinazolinedione hydrochloride TLC Rf=0.85
MS 462 (M+)

EXAMPLE 29

5,6-Benzo-2,4-diazo(2-(4-(5H-dibenzo[a,d]cyclohepten-5-ylidene)-1-piperidinyl)ethyl)tetrahydrothiopyrane hydrochloride TLC Rf=0.91
MS 498 (M+)

EXAMPLE 30

2-(4-(5H-Dibenzo[a,d]cyclohepten-5-ylidene)-1-piperidinyl)-1-(3,4-dimethoxyphenyl)ethane hydrochloride TLC Rf=0.78
MS 450 (M+)

EXAMPLE 31

5-(4-(5H-Dibenzo[a,d]cyclohepten-5-ylidene)-1-piperidinyl)-2-(3,4-dimethoxyphenyl)-2-isopropyl-valeronitrile hydrochloride TLC Rf=0.92
MS 532 (M+)
NMR 0.77 (3H, d), 1.18 (3H, d), 1.6–3.3 (15H, m), 3.86 (3H, s), 3.92 (3H, s), 6.8–7.4 (11H, m)

EXAMPLE 32

3-(4-(5H-Dibenzo[a,d]cyclohepten-5-ylidene)-1-piperidinyl)propyl-4-fluorophenylsulfoxide hydrochloride TLC Rf=0.78
MS 457 (M+)

EXAMPLE 33

3-(4-(5H-Dibenzo[a,d]cyclohepten-5-ylidene)-1-piperidinyl)propyl-4-fluorophenylsulfone hydrochloride TLC Rf=0.62
MS 473 (M+)

EXAMPLE 34

4-(5H-Dibenzo[a,d]cyclohepten-5-ylidene)-1-(3-(2-aminophenylthio)-1-propyl)piperidine hydrochloride TLC Rf=0.84
MS 439 (M+)

EXAMPLE 35

4-(5H-Dibenzo[a,d]cyclohepten-5-ylidene)-1-(1-(2-benzoylamino)ethyl)piperidine hydrochloride TLC Rf=0.84
MS 420 (M+)

EXAMPLE 36

4-(5H-Dibenzo[a,d]cyclohepten-5-ylidene)-1-(1-(2-N-phenylcarbamoylamino)ethyl)piperidine hydrochloride TLC Rf=0.55
MS 435 (M+)

EXAMPLE 37

1-(3-(2-Cinnamoylaminophenylthio)-1-propyl)-4-(5H-dibenzo[a,d]-cyclohepten-5-ylidene)piperidine hydrochloride TLC Rf=0.66
MS 568 (M+)
NMR (free base) 1.74 (2H, tt), 2.0–2.6 (8H, m), 2.80 (2H, t), 6.59 (1H, d), 6.88 (2H, s), 7.0–7.6 (16H, m), 7.75 (1H, d), 8.5 (1H, d), 8.68 (1H, bs)

EXAMPLE 38

1-Cinnamyl-4-(5H-dibenzo[a,d]cyclohepten-5-ylidene)piperidine hydrochloride

TLC Rf=0.84
MS 389 (M+)
NMR (free base) 2.1–2.7 (8H, m), 3.15 (2H, d), 6.25 (1H, td), 6.47 (1H, d), 6.90 (2H, s), 7.1–7.4 (13H, m)

EXAMPLE 39

5-(4-(5H-Dibenzo[a,d]cyclohepten-5-ylidene)-1-piperidinyl)-2-(3,4,5-trimethoxyphenyl)-2-isopropylvaleronitrile hydrochloride TLC Rf=0.80
MS 563 (M+)

EXAMPLE 40

2-(3-(4-(5H-Dibenzo[a,d]cyclohepten-5-ylidene)-1-piperidinyl)-1-propyl)-2-phenyl-1,3-dithiane-1,1,3,3-tetroxide hydrochloride TLC Rf=0.48
MS 573 (M+)

EXAMPLE 41

2-(3,4-Dimethoxyphenyl)-2-(3-(4-(5H-dibenzo[a,d]cyclohepten-5ylidene)-1-piperidinyl)-1-propyl)-1,3-dithiane-1,1,3,3-tetroxide hydrochloride TLC Rf=0.48
MS 573 (M+)

EXAMPLE 42

5-(4-(5H-Dibenzo[a,d]cyclohepten-5-ylidene)-1-piperidinyl)-2-(3,4-dichlorophenyl)-2-isopropylvaleronitrile hydrochloride TLC Rf=0.94
MS 540 (M+)

EXAMPLE 43

2-(3-Benzoylphenyl)-5-(4-(5H-dibenzo[a,d]cyclohepten-5-ylidene)-1-piperidinyl)-2-methylvaleronitrile hydrochloride TLC Rf=0.88
MS 548 (M+)

EXAMPLE 44

5-(4-(5H-Dibenzo[a,d]cyclohepten-5-ylidene)-1-piperidinyl)-2,2-diphenylvaleronitrile hydrochloride TLC Rf=0.74
MS 506 (M+)

EXAMPLE 45

4-(4-(5H-Dibenzo[a,d]cyclohepten-5-ylidene)-1-piperidinyl)-3,4-dimethoxybutyrophenone hydrochloride TLC Rf=0.61
MS 479 (M+)

EXAMPLE 46

6-(4-(5H-Dibenzo[a,d]cyclohepten-5-ylidene)-1-piperidinyl)-2-phenylhexanenitrile hydrochloride TLC Rf=0.86
MS 430 (M+)

EXAMPLE 47

6-(4-(5H-Dibenzo[a,d]cyclohepten-5-ylidene)-1-piperidinyl)-2-isopropyl-2-phenylhexanenitrile hydrochloride TLC Rf=0.88
MS 472 (M+)

EXAMPLE 48

6-(4-(5H-Dibenzo[a,d]cyclohepten-5-ylidene)-1-piperidinyl)-2-(3,4-dimethoxyphenyl)-2-isopropylhexanenitrile hydrochloride TLC Rf=0.81
MS 546 (M+)

EXAMPLE 49

7-(4-(5H-Dibenzo[a,d]cyclohepten-5-ylidene)-1-piperidinyl)-2-phenylheptanenitrile hydrochloride TLC Rf=0.84
MS 444 (M+)

EXAMPLE 50

7-(4-(5H-Dibenzo[a,d]cyclohepten-5-ylidene)-1-piperidinyl)-2-isopropyl-2-phenylheptanenitrile hydrochloride TLC Rf=0.84
MS 486 (M+)

EXAMPLE 51

7-(4-(5H-Dibenzo[a,d]cyclohepten-5-ylidene)-1-piperidinyl)-2-(3,4-dimethoxyphenyl)-2-isopropylheptanenitrile hydrochloride TLC Rf=0.86
MS 560 (M+)

EXAMPLE 52

2-(3-Chloropropyl)-5-(4-(5H-dibenzo[a,d]cyclohepten-5-ylidene)-1-piperidinyl)-2-phenylvaleronitrile hydrochloride TLC Rf=0.92
MS 506 (M+)

EXAMPLE 53

5-(4-(5H-Dibenzo[a,d]cyclohepten-5-ylidene)-1-piperidinyl)-2--phenyl-2-phenylthiovaleronitrile hydrochloride TLC Rf=0.81
MS 538 (M+)

EXAMPLE 54

5-(4-(5H-Dibenzo[a,d]cyclohepten-5-ylidene)-1-piperidinyl)-2-(3,4-dimethoxyphenyl)-2-phenylthiovaleronitrile hydrochloride TLC Rf=0.91
MS 598 (M+)

EXAMPLE 55

5-(4-(5H-Dibenzo[a,d]cyclohepten-5-ylidene)-1-piperidinyl)-2-(1-naphthyl)valeronitrile hydrochloride TLC Rf=0.85
MS 580 (M+)

EXAMPLE 56

5-(4-(5H-Dibenzo[a,d]cyclohepten-5-ylidene)-1-piperidinyl)-2-(1-naphthyl)-2-isopropylvaleronitrile hydrochloride TLC Rf=0.90
MS 522 (M+)

EXAMPLE 57

5-(4-(5H-Dibenzo[a,d]cyclohepten-5-ylidene)-1-piperidinyl)-2-(2-naphthyl)valeronitrile hydrochloride TLC Rf=0.85
MS 480 (M+)

EXAMPLE 58

5-(4-(5H-Dibenzo[a,d]cyclohepten-5-ylidene)-1-piperidinyl)-2-(2-naphthyl)-2-isopropylvaleronitrile hydrochloride TLC Rf=0.87
MS 522 (M+)

EXAMPLE 59

5-(4-(5H-Dibenzo[a,d]cyclohepten-5-ylidene)-1-piperidinyl)-2-(3-trifluoromethylphenyl)valeronitrile hydrochloride TLC Rf=0.72
MS 498 (M+)

EXAMPLE 60

5-(4-(5H-Dibenzo[a,d]cyclohepten-5-ylidene)-1-piperidinyl)-2-isopropyl-2-(3-trifluoromethylphenyl)-valeronitrile hydrochloride TLC Rf=0.75
MS 540 (M+)

EXAMPLE 61

8-(4-(5H-Dibenzo[a,d]cyclohepten-5-ylidene)-1-piperidinyl)-2-phenyloctanenitrile hydrochloride TLC Rf=0.84
MS 472 (M+)

EXAMPLE 62

8-(4-(5H-Dibenzo[a,d]cyclohepten-5-ylidene)-1-piperidinyl)-2-isopropyl-2-phenyloctanenitrile hydrochloride TLC Rf=0.88
MS 514 (M+)

EXAMPLE 63

8-(4-(5H-Dibenzo[a,d]cyclohepten-5-ylidene-1-piperidinyl)-2-(3,4-dimethoxyphenyl)-2-isopropyloctanenitrile hydrochloride TLC Rf=0.82
MS 574 (M+)

EXAMPLE 64

1-(3-(4-(5H-Dibenzo[a,d]cyclohepten-5-ylidene)-1-piperidinyl)-1-propyl)-1-indanenitrile hydrochloride TLC Rf=0.90
MS 456 (M+)

EXAMPLE 65

1-(3-(4-(5H-Dibenzo[a,d]cyclohepten-5-ylidene)-1-piperidinyl)-1-propyl)-5,6-dimethoxy-1-indanenitrile hydrochloride TLC Rf=0.85
MS 516 (M+)

EXAMPLE 66

5-(4-(5H-Dibenzo[a,d]cyclohepten-5-ylidene)-1-piperidinyl)-2-(1-methylpyrrol-2-yl)valeronitrile hydrochloride TLC Rf=0.61
MS 433 (M+)

EXAMPLE 67

5-(4-(5H-Dibenzo[a,d]cyclohepten-5-ylidene)-1-piperidinyl)-2-isopropyl-2-(1-methylpyrrol-2-yl)valeronitrile hydrochloride TLC Rf=0.71
MS 475 (M+)

EXAMPLE 68

5-(4-(5H-Dibenzo[a,d]cyclohepten-5-ylidene)-1-piperidinyl)-2-isopropyl-2-(pyrrol-2-yl)valeronitrile hydrochloride TLC Rf=0.55
MS 461 (M+)

EXAMPLE 69

5-(4-(5H-Dibenzo[a,d]cyclohepten-5-ylidene)-1-piperidinyl)-2-(3-α-hydroxybenzyl)phenyl)-2-methyl-valeronitrile hydrochloride TLC Rf=0.51
MS 550 (M+)

EXAMPLE 70

2-(3-Benzoylphenyl)-6-(4-(5H-Dibenzo[a,d]cyclohepten-5-ylidene)-1-piperidinyl)-2-methylhexanenitrile hydrochloride TLC Rf=0.88
MS 562 (M+)

EXAMPLE 71

6-(4-(5H-Dibenzo[a,d]cyclohepten-5-ylidene)-1-piperidinyl)-2-(3-α-hydroxybenzyl)-phenyl-2-methyl-hexanenitrile hydrochloride TLC Rf=0.52
MS 564 (M+)

EXAMPLE 72

2-(3-Benzoylphenyl)-7-(4-(5H-Dibenzo[a,d]cyclohepten-5-ylidene)-1-piperidinyl)-2-methylheptanenitrile hydrochloride TLC Rf=0.91
MS 576 (M+)

EXAMPLE 73

7-(4-(5H-Dibenzo[a,d]cyclohepten-5-ylidene)-1-piperidinyl)-2-(3-(α-hydroxybenzyl)phenyl-2-methyl-heptanenitrile hydrochloride TLC Rf=0.52
MS 578 (M+)

EXAMPLE 74

2-(3-Benzoylphenyl)-8-(4-(5H-Dibenzo[a,d]cyclohepten-5-ylidene)-1-piperidinyl)-2-methyloctanenitrile hydrochloride TLC Rf=0.90
MS 590 (M+)

EXAMPLE 75

8-(4-(5H-Dibenzo[a,d]cyclohepten-5-ylidene)-1-piperidinyl)-2-(3-(α-hydroxybenzyl)phenyl-2-methyloctanenitrile hydrochloride TLC Rf=0.61
MS 592 (M+)

EXAMPLE 76

5-(4-(5H-Dibenzo[a,d]cyclohepten-5-ylidene)-1-piperidinyl)-2-methyl-2-phenylvaleronitrile hydrochloride TLC Rf=0.91
MS 544 (M+)

EXAMPLE 77

5-(4-(5H-Dibenzo[a,d]cyclohepten-5-ylidene)-1-piperidinyl)-2-(3,4-dimethoxyphenyl)-2-methylvaleronitrile hydrochloride TLC Rf=0.85
MS 504 (M+)

EXAMPLE 78

5-(4-(5H-Dibenzo[a,d]cyclohepten-5-ylidene)-1-piperidinyl)-2-ethyl-2-phenylvaleronitrile hydrochloride TLC Rf=0.92
MS 458 (M+)

EXAMPLE 79

5-(4-(5H-Dibenzo[a,d]cyclohepten-5-ylidene)-1-piperidinyl)-2-(3,4-dimethoxyphenyl)-2-ethylvaleronitrile hydrochloride TLC Rf=0.90
MS 518 (M+)

EXAMPLE 80

5-(4-(5H-Dibenzo[a,d]cyclohepten-5-ylidene)-1-piperidinyl)-2-propyl-2-phenylvaleronitrile hydrochloride TLC Rf=0.93
MS 472 (M+)

EXAMPLE 81

5-(4-(5H-Dibenzo[a,d]cyclohepten-5-ylidene)-1-piperidinyl)-2-(3,4-dimethoxyphenyl)-2-propylvaleronitrile hydrochloride TLC Rf=0.91
MS 532 (M+)

EXAMPLE 82

2-Butyl-5-(4-(5H-Dibenzo[a,d]cyclohepten-5-ylidene)-1-piperidinyl)-2-phenylvaleronitrile hydrochloride TLC Rf=0.95
MS 486 (M+)

EXAMPLE 83

2-Butyl-5-(4-(5H-Dibenzo[a,d]cyclohepten-5-ylidene)-1-piperidinyl)-2-(3,4-dimethoxyphenyl)valeronitrile hydrochloride TLC Rf=0.90
MS 546 (M+)

EXAMPLE 84

5-(4-(5H-Dibenzo[a,d]cyclohepten-5-ylidene)-1-piperidinyl)-2-pentyl-2-phenylvaleronitrile hydrochloride TLC Rf=0.95
MS 500 (M+)

EXAMPLE 85

5-(4-(5H-Dibenzo[a,d]cyclohepten-5-ylidene)-1-piperidinyl)-2-(3,4-dimethoxyphenyl)-2-pentylvaleronitrile hydrochloride TLC Rf=0.92
MS 560 (M+)

EXAMPLE 86

5-(4-(5H-Dibenzo[a,d]cyclohepten-5-ylidene)-1-piperidinyl)-2-hexyl-2-phenylvaleronitrile hydrochloride TLC Rf=0.95
MS 514 (M+)

EXAMPLE 87

5-(4-(5H-Dibenzo[a,d]cyclohepten-5-ylidene)-1-piperidinyl)-2-(3,4-dimethoxyphenyl)-2-hexylvaleronitrile hydrochloride TLC Rf=0.92
MS 574 (M+)

EXAMPLE 88

5-(4-(5H-Dibenzo[a,d]cyclohepten-5-ylidene)-1-piperidinyl)-2-heptyl-2-phenylvaleronitrile hydrochloride TLC Rf=0.95
MS 528 (M+)

EXAMPLE 89

5-(4-(5H-Dibenzo[a,d]cyclohepten-5-ylidene)-1-piperidinyl)-2-(3,4-dimethoxyphenyl)-2-heptylvaleronitrile hydrochloride TLC Rf=0.91
MS 588 (M+)

EXAMPLE 90

5-(4-(5H-Dibenzo[a,d]cyclohepten-5-ylidene)-1-piperidinyl)-2-octyl-2-phenylvaleronitrile hydrochloride TLC Rf=0.94
MS 542 (M+)

EXAMPLE 91

5-(4-(5H-Dibenzo[a,d]cyclohepten-5-ylidene)-1-piperidinyl)-2-octylvaleronitrile hydrochloride TLC Rf=0.94
MS 602 (M+)

EXAMPLE 92

5-(4-(5H-Dibenzo[a,d]cyclohepten-5-ylidene)-1-piperidinyl)-2-nonyl-2-phenylvaleronitrile hydrochloride TLC Rf=0.95
MS 556 (M+)

EXAMPLE 93

5-(4-(5H-Dibenzo[a,d]cyclohepten-5-ylidene)-1-piperidinyl)-2-(3,4-dimethoxyphenyl)-2-nonylvaleronitrile hydrochloride TLC Rf=0.93
MS 616 (M+)

EXAMPLE 94

2-Decyl-5-(4-(5H-Dibenzo[a,d]cyclohepten-5-ylidene)-1-piperidinyl)-2-phenylvaleronitrile hydrochloride TLC Rf=0.95
MS 570 (M+)

EXAMPLE 95

2-Decyl-5-(4-(5H-Dibenzo[a,d]cyclohepten-5-ylidene)-1-piperidinyl)-2-(3,4-dimethoxyphenyl)valeronitrile hydrochloride TLC Rf=0.94
MS 630 (M+)

EXAMPLE 96

5-(4-(5H-Dibenzo[a,d]cyclohepten-5-ylidene)-1-piperidinyl)-acetophenone hydrochloride TLC Rf=0.71
MS 391 (M+)

EXAMPLE 97

2-(4-(5H-Dibenzo[a,d]cyclohepten-5-ylidene)-1-piperidinyl)-1-hydroxy-1-phenylethane hydrochloride TLC Rf=0.36
MS 393 (M+)

EXAMPLE 98

3-(4-(5H-Dibenzo[a,d]cyclohepten-5-ylidene)-1-piperidinyl)propiophenone hydrochloride TLC Rf=0.74
MS 405 (M+)

EXAMPLE 99

3-(4-(5H-Dibenzo[a,d]cyclohepten-5-ylidene)-1-piperidinyl)-1-hydroxy-1-phenylpropane hydrochloride TLC Rf=0.35
MS 407 (M+)

EXAMPLE 100

3-(4-(5H-Dibenzo[a,d]cyclohepten-5-ylidene)-1-piperidinyl)butyrophenone hydrochloride TLC Rf=0.75
MS 419 (M+)

EXAMPLE 101

4-(4-(5H-Dibenzo[a,d]cyclohepten-5-ylidene)-1-piperidinyl)-1-hydroxy-1-phenylbutane hydrochloride TLC Rf=0.39
MS 421 (M+)

EXAMPLE 102

5-(4-(5H-Dibenzo[a,d]cyclohepten-5-ylidene)-1-piperidinyl)valerophenone hydrochloride TLC Rf=0.76
MS 433 (M+)

EXAMPLE 103

5-(5H-Dibenzo[a,d]cyclohepten-5-ylidene)-1-piperidinyl)-1-hydroxy-1-phenylpentane hydrochloride TLC Rf=0.78
MS 447 (M+)

EXAMPLE 104

2-(4-(5H-Dibenzo[a,d]cyclohepten-5-ylidene)-1-piperidinyl)-4'-fluoroacetophenone hydrochloride TLC Rf=0.80
MS 409 (M+)

EXAMPLE 105

2-(4-(5H-Dibenzo[a,d]cyclohepten-5-ylidene)-1-piperidinyl)-1-hydroxy-1-(4-fluorophenyl)ethane hydrochloride TLC Rf=0.44
MS 411 (M+)

EXAMPLE 106

3-(4-(5H-Dibenzo[a,d]cyclohepten-5-ylidene)-1-piperidinyl)-4'-fluoropropiophenone hydrochloride TLC Rf=0.80
MS 423 (M+)

EXAMPLE 107

3-(4-(5H-Dibenzo[a,d]cyclohepten-5-ylidene)-1-piperidinyl)-1-hydroxy-1-(4-fluorophenyl)propane hydrochloride TLC Rf=0.44
MS 425 (M+)

EXAMPLE 108

4-(4-(5H-Dibenzo[a,d]cyclohepten-5-ylidene)-1-piperidinyl)-1-hydroxy-1-(4-fluorophenyl)butane hydrochloride TLC Rf=0.45
MS 439 (M+)

EXAMPLE 109

5-(4-(5H-Dibenzo[a,d]cyclohepten-5-ylidene)-1-piperidinyl)-4'-fluorovalerophenone hydrochloride TLC Rf=0.84
MS 451 (M+)

EXAMPLE 110

5-(4-(5H-Dibenzo[a,d]cyclohepten-5-ylidene)-1-piperidinyl)-1-hydroxy-1-(4-fluorophenyl)pentane hydrochloride TLC Rf=0.51
MS 453 (M+)

EXAMPLE 111

4-(5H-Dibenzo[a,d]cyclohepten-5-ylidene)-1-(2-fluorobenzyl)piperidine hydrochloride TLC Rf=0.75
MS 381 (M+)

EXAMPLE 112

4-(5H-Dibenzo[a,d]cyclohepten-5-ylidene)-1-(3-fluorobenzyl)piperidine hydrochloride TLC Rf=0.79
MS 381 (M+)

EXAMPLE 113

4-(5H-Dibenzo[a,d]cyclohepten-5-ylidene)-1-(4-fluorobenzyl)piperidine hydrochloride TLC Rf=0.61
MS 381 (M+)

EXAMPLE 114

4-(5H-Dibenzo[a,d]cyclohepten-5-ylidene)-1-(2-trifluoromethylbenzyl)piperidine hydrochloride TLC Rf=0.83
MS 431 (M+)

EXAMPLE 115

4-(5H-Dibenzo[a,d]cyclohepten-5-ylidene)-1-(3-trifluoromethylbenzyl)piperidine hydrochloride TLC Rf=0.82
MS 431 (M+)

EXAMPLE 116

5-(4-(5H-Dibenzo[a,d]cyclohepten-5-ylidene)-1-piperidine hydrochloride

TLC Rf=0.79
MS 431 (M+)

EXAMPLE 117

4-(5H-Dibenzo[a,d]cyclohepten-5-ylidene)-1-(2-methoxybenzyl)piperidine hydrochloride TLC Rf=0.61
MS 393 (M+)

EXAMPLE 118

4-(5H-Dibenzo[a,d]cyclohepten-5-ylidene)-1-(3-methoxybenzyl)piperidine hydrochloride TLC Rf=0.61
MS 393 (M+)

EXAMPLE 119

4-(5H-Dibenzo[a,d]cyclohepten-5-ylidene)-1-(4-methoxybenzyl)piperidine hydrochloride TLC Rf=0.52
MS 393 (M+)

EXAMPLE 120

4-(5H-Dibenzo[a,d]cyclohepten-5-ylidene)-1-pentafluorobenzylpiperidine hydrochloride TLC Rf=0.80
MS 453 (M+)

EXAMPLE 121

5-(4-(5H-Dibenzo[a,d]cyclohepten-5-ylidene)-1-piperidinyl)-2-phenylvaleronitrile hydrochloride TLC Rf=0.86
MS 440 (M+)

EXAMPLE 122

5-(4-(5H-Dibenzo[a,d]cyclohepten-5-ylidene)-1-piperidinyl)-2-isopropyl-2-phenylvaleronitrile hydrochloride TLC Rf=0.82
MS 488 (M+)

EXAMPLE 123

5-(4-(5H-Dibenzo[a,d]cyclohepten-5-ylidene)-1-piperidinyl-2-(3,4-dimethoxyphenyl)valeronitrile hydrochloride TLC Rf=0.75
MS 500 (M+)

EXAMPLE 124

2-(3-(4-(5H-Dibenzo[a,d]cyclohepten-5-ylidene)-1-piperidinyl)-1-propyl-2-(4-fluorophenyl)-1,3-dioxolane hydrochloride TLC Rf=0.68
MS 481 (M+)

EXAMPLE 125

4-(4-(5H-Dibenzo[a,d]cyclohepten-5-ylidene)-1-piperidinyl)-4'-fluorobutyrophenone hydrochloride TLC Rf=0.82
MS 437 (M+)

EXAMPLE 126

5-(4-(5H-Dibenzo[a,d]cyclohepten-5-ylidene)-1-piperidinyl)-2-isopropyl-2-(3,4,5-trimethoxyphenyl)-valeronitrile hydrochloride TLC Rf=0.66
MS 562 (M+)

| exp | compound | MD (M+) | TLC (Rf) | solvent |
|---|---|---|---|---|
| 127 | 2-(4-(5H-Dibenzo[a,d]cyclohepten-5-ylidene)-1-piperidinyl-1-(4-fluorophenyl)ethane hydrochloride | 395 | 0.55 | B |
| 128 | 1-(2-Chlorobenzyl)-4-(5H-Dibenzo[a,d]cyclohepten-5-ylidene)piperidine hydrochloride | 397 | 0.68 | B |
| 129 | 1-(3-Chlorobenzyl)-4-(5H-Dibenzo[a,d]cyclohepten-5-ylidene)piperidine hydrochloride | 397 | 0.58 | B |
| 130 | 1-(4-Chlorobenzyl)-4-(5H-Dibenzo[a,d]cyclohepten-5-ylidene)piperidine hydrochloride | 397 | 0.58 | B |
| 131 | 4-(5H-Dibenzo[a,d]cyclohepten-5-ylidene)-1-(2-methylbenyl)piperidine hydrochloride | 377 | 0.74 | B |
| 132 | 4-(5H-Dibenzo[a,d]cyclohepten-5-ylidene)-1-(3-methylbenyl)piperidine hydrochloride | 377 | 0.71 | B |
| 133 | 4-(5H-Dibenzo[a,d]cyclohepten-5-ylidene)-1-(4-methylbenyl)piperidine hydrochloride | 377 | 0.65 | B |
| 134 | 4-(5H-Dibenzo[a,d]cyclohepten-5-ylidene)-1-heptylpiperidine hydrochloride | 371 | 0.70 | B |
| 135 | 4-(5H-Dibenzo[a,d]cyclohepten-5-ylidene)-1-nondecylpiperidine hydrochloride | 399 | 0.75 | B |
| 136 | 4-(5H-Dibenzo[a,d]cyclohepten-5-ylidene)-1-undecylpiperidine hydrochloride | 427 | 0.75 | B |
| 137 | 4-(5H-Dibenzo[a,d]cyclohepten-5-ylidene)-1-tridecylpiperidine hydrochloride | 455 | 0.78 | B |
| 138 | 1-(2-Aminobenzy)-4-(5H-Dibenzo[a,d]cyclohepten-5-ylidene)piperidine dihydrochloride | 392 | 0.38 | B |
| 139 | 1-(3-Aminobenzyl)-4-(5H-Dibenzo[a,d]cyclohepten-5-ylidene)piperidine dihydrochloride | 392 | 0.23 | B |
| 140 | 1-(4-Aminobenzy)-4-(5H-Dibenzo[a,d]cyclohepten-5-ylidene)piperidine dihydrochloride | 392 | 0.26 | B |
| 141 | 4-(5H-Dibenzo[a,d]cyclohepten-5-ylidene)-1-(2-nitrobenzyl)piperidine hydrochloride | 422 | 0.85 | B |
| 142 | 4-(5H-Dibenzo[a,d]cyclohepten-5-ylidene)-1-(3-nitrobenzyl)piperidine hydrochloride | 422 | 0.82 | B |
| 143 | 4-(5H-Dibenzo[a,d]cyclohepten-5-ylidene)-1-(4-nitrobenzyl)piperidine hydrochloride | 422 | 0.83 | B |
| 144 | 5-(4-(5H-Dibenzo[ a,d]cyclohepten-5-ylidene)-1-piperidinyl)-2-(3-fluorophenyl)-2-isopropylvaleronitrile hydrochloride | 500 | 0.71 | B |

-continued

| exp | compound | MD (M+) | TLC (Rf) | solvent |
|---|---|---|---|---|
| 145 | 5-(4-(5H-Dibenzo[a,d]cyclohepten-5-ylidene)-1-piperidinyl)-2-isopropyl-2-(3-methoxyphenyl)valeronitrile hydrochloride | 512 | 0.64 | B |
| 146 | 5-(4-(5H-Dibenzo[a,d]cyclohepten-5-ylidene)-1-piperidinyl)-2-isopropyl-2-(3-methylphenyl)valeronitrile hydrochloride | 496 | 0.68 | B |
| 147 | 5-(4-(5H-Dibenzo[a,d]cyclohepten-5-ylidene)-1-piperidinyl)-2-isopropyl-2-(2-trifluoromethylphenyl)valeronitrile hydrochloride | 549 | 0.78 | B |
| 148 | 5-(4-(5H-Dibenzo[a,d]cyclohepten-5-ylidene)-1-piperidinyl)-2-isopropyl-2-(4-trifluoromethylphenyl)valeronitrile hydrochloride | 540 | 0.77 | B |
| 149 | 5-(4-(5H-Dibenzo[a,d]cyclohepten-5-ylidene)-1-piperidinyl)-2-ethyl-2-(3-trifluoromethylphenyl)valeronitrile hydrochloride | 526 | 0.77 | B |
| 150 | 2-Butyl-5-(4-(5H-Dibenzo[a,d]cyclohepten-5-ylidene)-1-piperidinyl)-2-(3-trifluoromethylphenyl)valeronitrile hydrochloride | 554 | 0.80 | B |
| 151 | 5-(4-(5H-Dibenzo[a,d]cyclohepten-5-ylidene)-1-piperidinyl)-2-hexyl-2-(3-trifluoromethylphenyl)valeronitrile hydrochloride | 582 | 0.80 | B |
| 152 | 4-(4-(5H-Dibenzo[a,d]cyclohepten-5-ylidene)-1-piperidinyl)-1-phenyl-1-butene hydrochloride | 403 | 0.51 | B |
| 153 | 1-Benzyloxy-2-(4-(5H-Dibenzo[a,d]cyclohepten-5-ylidene)-1-piperidinyl)ethane hydrochloride | 407 | 0.58 | B |
| 154 | 1-Cyclohexyl-6-(4-(5H-dibenzo[a,d]cyclohepten-5-ylidene)-1-piperidinyl)hexane hydrochloride | 439 | 0.62 | B |
| 155 | 1-Cyclohexyl-7-(4-(5H-dibenzo[a,d]cyclohepten-5-ylidene)-1-piperidinyl)heptane hydrochloride | 453 | 0.65 | B |
| 156 | 1-Cyclohexyl-8-(4-(5H-dibenzo[a,d]cyclohepten-5-ylidene)-1-piperidinyl)octane hydrochloride | 467 | 0.68 | B |
| 157 | 1-(4-Cyclohexylbutanoyl)-4-(5H-dibenzo[a,d]cyclohepten-5-ylidene)piperidine | 425 | 0.75 | B |
| 158 | 1-(2-Cyanobenzyl)-4-(5H-dibenzo[a,d]cyclohepten-5-ylidene)piperidine hydrochloride | 388 | 0.83 | B |
| 159 | 1-(3-Cyanobenzyl)-4-(5H-dibenzo[a,d]cyclohepten-5-ylidene)piperidine hydrochloride | 388 | 0.85 | B |
| 160 | 1-(4-Cyanobenzyl)-4-(5H-dibenzo[a,d]cyclohepten-5-ylidene)piperidine hydrochloride | 388 | 0.70 | B |
| 161 | 4-(5H-Dibenzo[a,d]cyclohepten-5-ylidene)-1-(2-Picolyl)piperidine dihydrochloride | 364 | 0.58 | B |
| 162 | 4-(5H-Dibenzo[a,d]cyclohepten-5-ylidene)-1-(3-Picolyl)piperidine dihydrochloride | 364 | 0.53 | B |
| 163 | 4-(5H-Dibenzo[a,d]cyclohepten-5-ylidene)-1-(4-Picolyl)piperidine dihydrochloride | 364 | 0.44 | B |
| 164 | 1-Decanolyl-4-(5H-dibenzo[a,d]cyclohepten-5-ylidene)piperidine | 427 | 0.75 | B |
| 165 | 1-Cyano-3-[4-(5H-Dibenzo[a,d]cyclohepten-5-ylidene)-1-piperidinyl)propane hydrochloride | 340 | 0.58 | B |
| 166 | 1-Cyano-4-[4-(5H-Dibenzo[a,d]cyclohepten-5-ylidene)-1-piperidinyl)propane hydrochloride | 354 | 0.52 | B |
| 167 | 2-(4-(5H-Dibenzo[a,d]cyclohepten-5-ylidene)-1-piperidinyl)-3',4'-dimethoxyacetophenone hydrochloride | 451 | 0.85 | B |
| 168 | 3-(4-(5H-Dibenzo[a,d]cyclohepten-5-ylidene)-1-piperidinyl)-3',4'-dimethoxyptiophenone hydrochloride | 465 | 0.61 | B |
| 169 | 5-(4-(5H-Dibenzo[a,d]cyclohepten-5-ylidene)-1-piperidinyl)-3',4'-dimethoxyvalerophenone hydrochloride | 193 | 0.64 | B |
| 170 | 4-(4-(5H-Dibenzo[a,d]cyclohepten-5-ylidene)-1-piperidinyl)-3',4',5'-trimethoxybutryrophenone hydrochloride | 509 | 0.82 | B |
| 171 | 4-(4-(5H-Dibenzo[a,d]cyclohepten-5-ylidene)-1-piperidinyl)-2',3',4'-trimethoxybutyrophenone hydrochloride | 509 | 0.86 | B |
| 172 | 4-(4-(5H-Dibenzo[a,d]cyclohepten-5-ylidene)-1-piperidinyl)-4'-methoxybutyrophenone hydrochloride | 449 | 0.61 | B |
| 173 | 4-(5H-Dibenzo[a,d]cyclohepten-5-ylidene)-1-(2,3-dimethoxybenzyl)piperidine hydrochloride | 423 | 0.63 | B |
| 174 | 4-(5H-Dibenzo[a,d]cyclohepten-5-ylidene)-1-(3,4-dimethoxybenzyl)piperidine hydrochloride | 423 | 0.73 | B |
| 175 | 4-(5H-Dibenzo[a,d]cyclohepten-5-ylidene)-1-(3,4-dimethoxybenzyl)piperidine | 437 | 0.58 | B |
| 176 | 1-Cyclohexyl-3-(4-(5H-dibenzo[a,d]cyclohepten-5-ylidene)-1-piperidinyl)propylketone hydrochloride | 425 | 0.51 | B |
| 177 | 2-Cyclohexyl-5-(4-(5H-dibenzo[a,d]cyclohepten-5-ylidene)-1-piperidinyl)valeronitrile hydrochloride | 436 | 0.60 | B |
| 178 | 1-(4-(3-Chloro-5H-dibenzo[a,d]cyclohepten-5-ylidene-1-piperidinyl)-4-cyclohexylbutane hydrochloride | 445 | 0.62 | B |
| 179 | 1-Cyclohexyl-4-(3-methoxy-5H-dibenzo[a,d]cyclohepten-5-ylidene)-1-piperidinyl)butane hydrochloride | 441 | 0.59 | B |
| 180 | 4,9-Dihydro-4-(1-(4-cyclohexylbutyl)-4-piperidinylidene-10H-benzo[4,5]cyclohepta[1,2-b]thiophen-10-one hydrochloride | 433 | 0.45 | B |
| 181 | 1-(4-Cyclohexylbutyl-4-(9-xantylidene)piperidine hydrochloride | 401 | 0.64 | B |
| 182 | 1-(4-Cyclohexylbutyl-4-(9-thioxantylidene)piperidine hydrochloride | 417 | 0.65 | B |
| 183 | 6,11-Dihydro-11-(1-(4-cyclohexylbutyl)-4-piperidinylidene-5H-dibenzo[5,6]cycloheptal[1,2-b]pyridine dihydrochloride | 414 | 0.41 | B |
| 184 | 4-(10,11-dihydro-5H-dibenzo[a,d]cyclohepten-5-ylidene)-1-(3-methoxybenzyl)piperidine hydrochloride | 395 | 0.73 | B |
| 185 | 1-Decyl-4-(10,11-Dihydro-5H-dibenzo[a,d]cyclohepten-5-ylidene)piperidine hydrochloride | 415 | 0.52 | B |
| 186 | 1-Cyclohexyl-4-(4-(10,11-Dihydro-5H-dibenzo[a,d]cycloheptan-5-ylidene)-1-piperidinyl)butane hydrochloride | 413 | 0.67 | B |
| 187 | 4-(4-(10,11-Dihydro-5H-dibenzo[a,d]cyclohepten-5-ylidene)-1-piperidinyl)-3',4'-dimethoxy-butyrophenone hydrochloride | 481 | 0.66 | B |
| 188 | 4-(5H-Dibenzo[a,d]cyclohepten-5-ylidene)-1-(3,4,5-trimethoxybenzyl)piperidine | 453 | 0.69 | B |
| 189 | 4-(5H-Dibenzo[a,d]cyclohepten-5-ylidene)-1-(3,4,5-trimethoxybenzoyl)piperidine | 467 | 0.71 | B |
| 190 | 4-(5H-Dibenzo[a,d]cyclohepten-5-ylidene)-1-(2-methylbenzoyl)piperidine | 391 | 0.73 | B |
| 191 | 4-(5H-Dibenzo[a,d]cyclohepten-5-ylidene)-1-(2-(4-fluorophenyl)acetyl)piperidine | 409 | 0.76 | B |
| 192 | 4-(5H-Dibenzo[a,d]cyclohepten-5-ylidene)-1-(2-dimethoxycinnamoyl)piperidine | 463 | 0.73 | B |
| 193 | 4-(5H-Dibenzo[a,d]cyclohepten-5-ylidene)-1-(2-dimethoxycinnamyl)piperidine hydrochloride | 449 | 0.46 | B |
| 194 | 4-(4-(5H-Dibenzo[a,d]cyclohepten-5-ylidene)-1-piperidinyl)-3',4'-diethoxybutyrophenone hydrochloride | 501 | 0.49 | B |
| 195 | 1-(4-(4-Aminophenyl)butyl)-4-(5H-dibenzo[a,d]cyclohepten-5-ylidine)piperidine dihydrochloride | 420 | 0.34 | B |
| 196 | 4-(5H-Dibenzo[a,d]cyclohepten-5-ylidene)-1-(4-(4-nitrophenyl)buytl)piperidine hydrochloride | 450 | 0.50 | B |
| 197 | 1-(4-(4-Acetylaminophenyl)butyl-4-(5H-dibenzo[a,d]cyclohepten-5-ylidine)piperidine dihydrochloride | 462 | 0.48 | B |
| 198 | 4-(4-(5H-Dibenzo[a,d]cyclohepten-5-ylidene)-1-piperidinyl)-3',4'-dimethylbutyrophenone hydrochloride | 447 | 0.53 | B |
| 199 | Ethyl 4-(4-(5H-dibenzo[a,d]cyclohepten-5-ylidene)-1-piperidinyl)butyrate hydrochloride | 387 | 0.51 | B |
| 200 | 4-((5H-Dibenzo[a,d]cyclohepten-5-ylidene)-1-piperidinyl)butyric acid | 359 | 0.15 | B |
| 201 | 4-(5H-Dibenzo[a,d]cyclohepten-5-ylidene)-1-(-3-(3',4'-dimethoxyphenyl)propyl)piperidine hydrochloride | 451 | 0.60 | B |
| 202 | 4-(5H-Dibenzo[a,d]cyclohepten-5-ylidene)-1-(3-(3',4'-dimethoxyphenyl)propanoyl)piperidine | 465 | 0.78 | B |
| 203 | 1-(4-(4-(5H-Dibenzo[a,d]cyclohepten-5-ylidene)-1-piperidinyl)butanoyl)piperidine hydrochloride | 426 | 0.60 | B |
| 204 | N-(4-(4-(5H-Dibenzo[a,d]cyclohepten-5-ylidene)-1-piperidinyl)butanoyl)-1,2,3,4-tetrahydroisoquinoline hydrochloride | 474 | 0.42 | B |
| 205 | 4-(4-(5H-Dibenzo[a,d]cyclohepten-5-ylidene)-1-piperidinyl)-1-(3,4-dimethoxy)phenyl-1-hydroxybutane hydrochloride | 481 | 0.38 | B |
| 206 | 1-Acetoxy-4-(4-(5H-dibenzo[a,d]cyclohepten-5-ylidene)-1-piperidinyl)-1-(3,4-dimethoxy)phenylbutane hydroxybutane hydrochloride | 523 | 0.49 | B |
| 207 | 1-Butyl-4-(4-(5H-Dibenzo[a,d]cyclohepten-5-ylidene)-1-piperidinyl)-1-(3,4-dimethoxy)phenyl-1- | 537 | 0.45 | B |

-continued

| exp | compound | MD (M+) | TLC (Rf) | solvent |
|---|---|---|---|---|
| | hydroxybutane hydroxybutane hydrochloride | | | |
| 208 | 1-(4-Methoxyxyxlohexyl)-4-(4-(5H-dibenzo[a,d]cyclohepten-5-ylidene)-1-piperidinyl)butane hydrochloride | 441 | 0.55 | B |
| 209 | 1-(4-(4-(5H-Dibenzo[a,d]cyclohepten-5-ylidene)-1-piperidinyl)butyl)piperidine dihydroxybutane hydrochloride | 412 | 0.03 | B |
| 210 | 4-(5H-Dibenzo[a,d]cyclohepten-5-ylidene)-1-(4-(N-imidazolylmethyl)cinnamyl)piperidine dihydroxybutane hydrochloride | 469 | 0.44 | B |
| 211 | 4-(5H-Dibenzo[a,d]cyclohepten-5-ylidene)-1-(2-naphthoyl)piperidine | 427 | 0.88 | B |
| 212 | 4-(5H-Dibenzo[a,d]cyclohepten-5-ylidene)-1-(2-naphthylmethyl)piperidine hydrochloride | 413 | 0.94 | B |
| 213 | 4-(5H-Dibenzo[a,d]cyclohepten-5-ylidene)-1-(1-naphthoyl)piperidine | 427 | 0.59 | B |
| 214 | 4-(5H-Dibenzo[a,d]cyclohepten-5-ylidene)-1-(1-naphthylmethyl)piperidine hydrochloride | 413 | 0.83 | B |
| 215 | 2-(4-(4-(5H-Dibenzo[a,d]cyclohepten-5-ylidene)-1-piperidinyl)butyl)cyclohexanone hydrochloride | 426 (H+) | 0.50 | B |
| 216 | 1-(4-(4-(5H-Dibenzo[a,d]cyclohepten-5-ylidene)-1-piperidinyl)butanoyl)-4-hydroxypiperidine hydrochloride | 442 | 0.58 | B |
| 217 | 1-(4-(4-(5H-Dibenzo[a,d]cyclohepten-5-ylidene)-1-piperidinyl)butanoyl)-4-ethoxyxarbonpiperidine hydrochloride | 499 | 0.26 | B |
| 218 | Cyclohexyl 3-(4-(5H-Dibenzo[a,d]cyclohepten-5-ylidene)-1-piperidinyl)propylether hydrochloride | 413 | 0.48 | B |
| 219 | 1-(4-(4-(5H-Dibenzo[a,d]cyclohepten-5-ylidene)-1-piperidinyl)-1-butyl)-1-methoxycarbonylcyclohexane hydrochloride | 470 (H+) | 0.55 | B |
| 220 | Ethyl 2-cyclohexyl-5-(4-(5H-Dibenzo[a,d]cyclohepten-5-ylidene)-1-piperidinyl)valerate hydrochloride | 483 | 0.65 | B |
| 221 | 4-(5H-Dibenzo[a,d]cyclohepten-5-ylidene)-1-(4-(3',4'-dimethoxyphenyl)butyl)piperidine hydrochloride | 465 | 0.66 | B |
| 222 | 2-(3-(4-(5H-Dibenzo[a,d]cyclohepten-5-ylidene)-1-piperidinyl)-1-propyl-2-(3,4-dimethoxyphenyl)-1,3-dioxolane hydrochloride | 523 | 0.54 | B |
| 223 | 1-Carboxyl-1-(4-(4-(5H-Dibenzo[a,d]cyclohepten-5-ylidene)-1-piperidinyl)butylcyclohexane hydrochloride | 456 (H+) | 0.38 | B |
| 224 | 4-(5H-Dibenzo[a,d]cyclohepten-5-ylidene)-1-(1,2,3,4-tetrahydro-2-naphthoyl)piperidine | 431 | 0.90 | B |
| 225 | 4-(5H-Dibenzo[a,d]cyclohepten-5-ylidene)-1-(1,2,3,4-tetrahydro-2-naphthylmethyl)piperidine | 417 | 0.55 | B |
| 226 | N-(3-(4-(5H-Dibenzo[a,d]cyclohepten-5-ylidene)-1-piperidinyl)propanoyl)cyclohexylamine hydrochloride | 426 | 0.64 | B |
| 227 | 2-(4-(5H-Dibenzo[a,d]cyclohepten-5-ylidene)-1-piperidinyl)ethyl cyclohexanecarboxylate hydrochloride | 427 | 0.71 | B |
| 228 | 4-(5H-Dibenzo[a,d]cyclohepten-5-ylidene)-1-cyclohexylbutane hydrochloride | 431 | 0.74 | B |
| 229 | 4-(5H-Dibenzo[a,d]thiepin-5-ylidene)-1-piperidinyl)-3+,4+-dimethoxybutyrophenone hydrochloride | 499 | 0.46 | B |
| 230 | 4-(5H-Dibenzo[a,d]cyclohepten-5-ylidene)-1-(2-nitrocinnamyl)piperidine hydrochloride | 434 | 0.70 | B |
| 231 | 1-(4-Aminocinnamyl)-4-(5H-dibenzo[a,d]cyclohepten-5-ylidene)piperidine hydrochloride | 404 | 0.36 | B |
| 232 | 1-(4-Acetylaminocinnamyl)-4-(5H-dibenzo[a,d]cyclohepten-5-ylidene)piperidine dihydrochloride | 446 | 0.27 | B |
| 233 | 4-(4-(5H-Dibenzo[a,d]cyclohepten-5-ylidene)-1-piperidinyl)-1-(2-furyl)-1-butanone hydrochloride | 409 | | B |
| 234 | 4-(4-(5H-Dibenzo[a,d]cyclohepten-5-ylidene)-1-piperidinyl)-1-(2-thienyl)-1-butanone hydrochloride | 425 | | B |
| 235 | 3-(4-(5H-Dibenzo[a,d]cyclohepten-5-ylidene)-1-piperidinyl)-1-propyl(2-tetrahydropyranyl)ether hydrochloride | 415 | 0.55 | B |
| 236 | Cyclohexyl 3-(4-(5H-Dibenzo[a,d]cyclohepten-5-ylidene)-1-piperidinyl)propionate hydrochloride | 427 | 0.71 | B |
| 237 | N-(2-(5H-Dibenzo[a,d]cyclohepten-5-ylidene)-1-piperidinyl)ethyl-4-nitrobenzamide hydrochloride | 465 | 0.49 | H |
| 238 | 2-Cyclohexyl-4-(4-(5H-dibenzo[a,d]cyclohepten-5-ylidene)-1-piperidinyl)butyric acid | 455 | 0.26 | B |
| 239 | 3-(4-(5H-Dibenzo[a,d]cyclohepten-5-ylidene)-1-piperidinyl)-1-propyl phenylsulphoxide hydrochloride | 409 | 0.29 | H |
| 240 | 2-(2-(4-(5H-Dibenzo[a,d]cyclohepten-5-ylidene)-1-piperidinyl)-1-ethyl-5',6'-dimethoxyindan hydrochloride | 477 | 0.41 | B |
| 241 | 3-(4-(5H-Dibenzo[a,d]cyclohepten-5-ylidene)-1-piperidinyl)-1-propyl phenylsulphone hydrochloride | 441 | 0.36 | B |
| 242 | N-(2-(5H-Dibenzo[a,d]cyclohepten-5-ylidene)-1-piperidinyl)ethyl-3',4'-dimethoxybenzamide hydrochloride | 480 | 0.44 | G |
| 243 | N-(2-(5H-Dibenzo[a,d]cyclohepten-5-ylidene)-1-piperidinyl)ethyl cyclohexanecarboxamide hydrochloride | 426 | 0.75 | B |
| 244 | N-(2-(5H-Dibenzo[a,d]cyclohepten-5-ylidene)-1-piperidinyl)ethyl isonicotinamide hydrochloride | 421 | 0.20 | B |
| 245 | 1-(4-(4-(5H-Dibenzo[a,d]cyclohepten-5-ylidene)-1-piperidinyl)butanoyl)morpholine hydrochloride | 428 | 0.31 | C |
| 246 | 1-(4-(4-(5H-Dibenzo[a,d]cyclohepten-5-ylidene)-1-piperidinyl)butanoyl)thiomorpholine hydrochloride | 444 | 0.43 | C |
| 247 | 3-(4-(5H-Dibenzo[a,d]cyclohepten-5-ylidene)-1-piperidinyl)-1-(4-notrophenyl)propane hydrochloride | 436 | 0.34 | H |
| 248 | 1-(4-Aminophenyl)-3-(4-(5H-Dibenzo[a,d]cyclohepten-5-ylidene)-1-piperidinyl)propane dihydrochloride | 406 | 0.33 | B |
| 249 | 1-(4-Acetylaminophenyl)-3-(4-(5H-Dibenzo[a,d]cyclohepten-5-ylidene)-1-piperidinyl)propane dihydrochloride | 448 | 0.43 | B |
| 250 | 3-(4-(5H-Dibenzo[a,d]cyclohepten-5-ylidene)-1-piperidinyl)-1-(2-nitrophenyl)propane hydrochloride | 436 | 0.53 | H |
| 251 | 1-(2-Aminophenyl)-3-(4-(5H-Dibenzo[a,d]cyclohepten-5-ylidene)-1-piperidinyl)propane dihydrochloride | 406 | 0.52 | B |
| 252 | 1-(2-Acetylaminophenyl)-3-(4-(5H-Dibenzo[a,d]cyclohepten-5-ylidene)-1-piperidinyl)propane dihydrochloride | 448 | 0.51 | B |
| 253 | 2-(4-(5H-Dibenzo[a,d]cyclohepten-5-ylidene)-1-piperidinyl)-1-ethylphenylsulphoxide hydrochloride | 425 | 0.20 | H |
| 254 | 2-(4-(5H-Dibenzo[a,d]cyclohepten-5-ylidene)-1-piperidinyl)-1-ethyl phenylsulphone hydrochloride | 455 | 0.71 | B |
| 255 | 4-(4-(5H-Dibenzo[a,d]cyclohepten-5-ylidene)-1-piperidinyl)-1-(2-nitrophenyl)butane hydrochloride | 450 | 0.49 | H |
| 256 | Cyclohexyl-3-(4-(5H-Dibenzo[a,d]cyclohepten-5-ylidene)-1-piperidinyl)-1-propylsulphide hydrochloride | 430 (H+) | 0.17 | J |
| 257 | Cyclohexyl-3-(4-(5H-Dibenzo[a,d]cyclohepten-5-ylidene)-1-piperidinyl)-1-propylsulphoxide hydrochloride | 445 | 0.51 | B |
| 258 | Cyclohexyl-3-(4-(5H-Dibenzo[a,d]cyclohepten-5-ylidene)-1-piperidinyl)-1-propylsulphone hydrochloride | 462 (H+) | 0.28 | H |
| 259 | Ethyl 2-cyclohexylmethyl-4-(4-(5H-dibenzo[a,d]cyclohepten-5-ylidene)-1-piperidinyl)butyrate hydrochloride | 483 | 0.70 | B |
| 260 | 1-(4-acetylamino-1-cyclohexyl)-4-(4-(5H-dibenzo[a,d]cyclohepten-5-ylidene)-1-piperidinyl)butane hydrochloride | 468 | 0.43 | B |
| 261 | 2-(2-(4-Dibenzo[a,d]cyclohepten-5-ylidene)-1-piperidinyl)-1-ethyl)-5',6'-dimethoxy-1-indanone hydrochloride | 477 | 0.41 | B |
| 262 | Ethyl 2-(2-cyclohexylethyl-3-(4-(5H-dibenzo[a,d]cyclohepten-5-ylidene)-1-piperidinyl)propionate hydrochloride | 483 | 0.74 | B |
| 263 | Cyclohexylmethyl-2-(4-(5H-Dibenzo[a,d]cyclohepten-5-ylidene)-1-piperidinyl)ethylsulfone hydrochloride | 461 | 0.94 | B |
| 264 | Cyclohexylmethyl-2-(4-(5H-Dibenzo[a,d]cyclohepten-5-ylidene)-1-piperidinyl)-1-ethylsulfoxide hydrochloride | 441 (H+) | 0.48 | B |
| 265 | Cyclohexylmethyl-2-(4-(5H-Dibenzo[a,d]cyclohepten-5-ylidene)-1-piperidinyl)-1-ethylsulfide hydrochloride | 429 | 0.85 | B |
| 266 | 2-(4-(5H-Dibenzo[a,d]cyclohepten-5-ylidene)-1-piperidinyl)-4-amino-6,7-dimethoxyquinazoline dihydrochloride | 476 | 0.34 | B |
| 267 | N-Acetyl-N-(3-(4-(5H-Dibenzo[a,d]cyclohepten-5-ylidene)-1-piperidinyl)-1-propyl)cyclohexylamine | 454 | 0.35 | B |

-continued

| exp | compound | MD (M+) | TLC (Rf) | solvent |
|---|---|---|---|---|
| | hydrochloride | | | |
| 268 | N-(4-(4-(5H-Dibenzo[a,d]cyclohepten-5-ylidene)-1-piperidinyl)-1-butyl)-2-piperidone hydrochloride | 426 | 0.39 | B |
| 269 | 1-(4-(4-(5H-Dibenzo[a,d]cyclohepten-5-ylidene)-1-piperidinyl)-1-butyl)-1-ethoxycarbonylcyclohexane hydrochloride | 483 | 0.82 | B |
| 270 | 3-(4-(5H-Dibenzo[a,d]cyclohepten-5-ylidene)-1-piperidinyl)-1-(3-pyridyl)propane dihydrochloride | 392 | 0.44 | B |
| 271 | 4-(4-(5H-Dibenzo[a,d]cyclohepten-5-ylidene)-1-piperidinyl)-3',4'-dimethoxybutyrophenone N-oxide | 477 (M-18) | 0.45 | B |
| 272 | 1-(4-(4-(5H-Dibenzo[a,d]cyclohepten-5-ylidene)-1-piperidinyl)-1-butyl)-1-hydroxymethylcyclohexane hydrochloride | 441 | 0.55 | B |
| 273 | 1-Acetoxymethyl-1-(4-(4-(5H-dibenzo[a,d]cyclohepten-5-ylidene)-1-piperidinyl)-1-butyl)cyclohexane hydrochloride | 483 | 0.86 | B |
| 274 | 4-(4-(5H-Dibenzo[a,d]cyclohepten-5-ylidene)-1-piperidinyl)-2-methyl-3',4'-dimethoxybutyrophenone hydrochloride | 493 | 0.22 | B |
| 275 | 4-(4-(5H-Dibenzo[a,d]cyclohepten-5-ylidene)-1-piperidinyl)-2-(2-propyl)-3',4'-dimethoxybutyrophenone hydrochloride | 521 | 0.28 | H |
| 276 | 2-Allyl-4-(4-(5H-dibenzo[a,d]cyclohepten-5-ylidene)-1-piperidinyl)-3',4'dimethoxybutyrophenone hydrochloride | 519 | 0.30 | H |
| 277 | 4-(4-(5H-dibenzo[a,d]cyclohepten-5-ylidene)-1-piperidinyl)-2-(1-propyl)-3',4'-dimethoxybutyrophenone hydrochloride | 521 | 0.38 | H |
| 278 | 4-(4-(5H-dibenzo[a,d]cyclohepten-5-ylidene)-1-piperidinyl)-2-ethyl-3',4'-dimethoxybutyrophenone hydrochloride | 507 | 0.33 | H |
| 279 | Cyclohexylmethyl-2-(4-(5H-Dibenzo[a,d]cyclohepten-5-ylidene)-1-piperidinyl)-2-ethyl)ether hydrochloride | 413 | 0.73 | B |
| 280 | 1-(n-Acetyl-3-piperidinyl)-3-(4-(5H-Dibenzo[a,d]cyclohepten-5-ylidine)-1-piperidinyl)propane hydrochloride | 440 | 0.75 | B |
| 281 | 3-(4-(5H-Dibenzo[a,d]cyclohepten-5-ylidine)-1-piperidinyl)-1-(3-piperiidinyl)propane dihydrochloride | 398 | 0.16 | A |
| 282 | 1-(3-Acetylamino-4-methoxyphenyl)-4-(4-(5H-dibenzo[a,d]cyclohepten-5-ylidine)-1-piperidinyl)butane hydrochloride | 492 | 0.58 | B |
| 283 | 4-(4-(5H-Dibenzo[a,d]cyclohepten-5-ylidine)-1-piperidinyl)-1-butyl)cyclohexane hydrochloride | 425 | 0.63 | B |
| 284 | 3-(4-(5H-Dibenzo[a,d]cyclohepten-5-ylidene)-1-piperidinyl)-1-(2-pyridyl)-1-propene hdiydrochloride | 390 | 0.66 | H |
| 285 | 2,6-Dimethyl-4-(4-(4-(5H-dibenzo[a,d]cyclohepten-5-ylidine)-1-piperidinyl)butyl)-5-methyl-1,4-dihydropyrydine-3,5-dicarboxylate hydrochloride | 528 | 0.30 | F |
| 286 | 3-(4-(5H-Dibenzo[a,d]cyclohepten-5-ylidene)-1-piperidinyl)-1-(2,3-dimethoxyphenyl)propane hydrochloride | 451 | 0.68 | H |
| 287 | 2-(4-(5H-Dibenzo[ a,d]cyclohepten-5-ylidene)-1-piperidinyl)methyl-5',6'-dimethoxyindan hydrochloride | 463 | 0.59 | H |
| 288 | 2,6-Dimethyl-4-(4-(4-(5H-Dibenzo[a,d]cyclohepten-5-ylidene)-1-piperidinyl)-1-butyl)-5-methylpyridine-3,5-dicarboxylate dihydrochloride | 527 | 0.68 | B |
| 289 | 3-(4-(5H-Dibenzo[a,d]cyclohepten-5-ylidene)-1-piperidinyl)-1-(4-pyridyl)propane dihydrochloride | 392 | 0.37 | B |
| 290 | N-(2-(5H-Dibenzo[a,d]cyclohepten-5-ylidine)-1-piperidinyl)ethyl-3-nitrobenzamide hydrochloride | 466 (H+) | 0.48 | D |
| 291 | N-(2-(5H-Dibenzo[a,d]cyclohepten-5-ylidine)-1-piperidinyl)ethyl-2-nitrobenzamide hydrochloride | 466 (H+) | | D |
| 292 | N-(2-(5H-Dibenzo[a,d]cyclohepten-5-ylidine)-1-piperidinyl)ethyl-3,4-dimethoxybenzamide hydrochloride | 481 (H+) | 0.31 | D |
| 293 | 4-(4-(5H-Dibenzo[a,d]cyclohepten-5-ylidine)-1-piperidinyl)-1-(2-pyrolle)-1-butane hydrochloride | 409 (H+) | | B |
| 294 | 1-(N-Acetyl-2-piperidinyl)-3-(4-(5H-dibenzo[a,d]cyclohepten-5-ylidine)-1-piperidinyl)propane hydrochloride | 440 | 0.30 | B |
| 295 | 4-(4-(5H-Dibenzo[a,d]cyclohepten-5-ylidene)-1-piperidinyl)-1-(N-methyl-3-piperidinyl)butane dihydrochloride | 426 | 0.07 | B |
| 296 | 1-(1-(4-Hydroxy)cyclohexyl)-4-(4-(5H-dibenzo[a,d]cyclohepten-5-ylidene)-1-piperidinyl)butane hydrochloride | 427 | 0.45 | B |
| 297 | 1-(1-(4-Cyano)cyclohexyl)-4-(4-(5H-Dibenzo[a,d]cyclohepten-5-ylidene)-1-piperidinyl)butane hydrochloride | 436 | 0.55 | F |
| 298 | 3-(4-(5H-Dibenzo[a,d]cyclohepten-5-ylidene)-1-piperidinyl)-1-(2-methoxyphenyl)propane hydrochloride | 421 | 0.81 | B |
| 299 | 1-(1-(3-Methoxy)cyclohexyl)-4-(4-(5H-Dibenzo[a,d]cyclohepten-5-ylidene)-1-piperidinyl)butane hydrochloride | 441 | 0.71 | B |
| 300 | 1-(1-(3-Hydroxyoxy)cyclohexyl)-4-(4-(5H-dibenzo[a,d]cyclohepten-5-ylidene)-1-piperidinyl)butane hydrochloride | 427 | 0.47 | B |
| 301 | 3-(4-(4-(5H-Dibenzo[a,d]cyclohepten-5-ylidene)-1-piperidinyl)-1-butyl)cyclohexanoe hydrochloride | 425 | 0.70 | B |
| 302 | 4-(5H-Dibenzo[a,d]cyclohepten-5-ylidene)-1-(2-nitrocinnamyl)piperidine hydrochloride | 434 | 0.91 | B |
| 303 | 1-(2-Aminocinnamyl)-4-(5H-dibenzo[a,d]cyclohepten-5-ylidene)piperidine hydrochloride | 404 | 0.62 | B |
| 304 | 1-(2-Acetylaminocinnamyl)-4-(5H-Dibenzo[a,d]cyclohepten-5-ylidene)piperidine hydrochloride | 446 | 0.55 | B |
| 305 | 4-(4-(4-(5H-Dibenzo[a,d]cyclohepten-5-ylidene)-1-piperidinyl)-1-butyl)tetrahydropyran hydrochloride | 413 | 0.69 | B |
| 306 | 4-(5H-Dibenzo[a,d]cyclohepten-5-ylidene)-1-(3-nitrocinnamyl)piperidine hydrochloride | 984 | 0.90 | B |
| 307 | 3-(4-(5H-Dibenzo[a,d]cyclohepten-5-ylidene)-1-piperidinyl)-1-(2-piperidinyl)propane dihydrochloride | 398 | 0.07 | A |
| 308 | 1-(N-Acetyl-4-piperidinyl)-3-(4-(5H-dibenzo[a,d]cyclohepten-5-ylidene)-1-piperidinyl)propane hydrochloride | 440 | 0.23 | H |
| 309 | 3-(4-(5H-Dibenzo[a,d]cyclohepten-5-ylidene)-1-piperidinyl)-1-(4-piperidinyl)propane dihydrochloride | 398 | 0.03 | B |
| 310 | 2-(2-(4-(5H-Dibenzo[a,d]cyclohepten-5-ylidene)-1-piperidinyl)-1-ethyl)indane hydrochloride | 417 | 0.59 | B |
| 311 | 4-(2-(4-(5H-Dibenzo[a,d]cyclohepten-5-ylidene)-1-piperidinyl)-1-ethyl)-2,4,5,6-tetramethyl-1,4-dihydropyridine-3,5-dicarboxylate hydrochloride | 524 | 0.68 | B |
| 312 | 4-(4-(5H-Dibenzo[a,d]cyclohepten-5-ylidene)-1-piperidinyl)-1-(N-ethoxycarbonyl-3-piperidinyl)butane hydrochloride | 484 | 0.64 | B |
| 313 | 1-(5-(4-(5H-Dibenzo[a,d]cyclohepten-5-ylidene)-1-piperidinyl)-1-pentyl)-1-methoxycarbonylcyclohexane hydrochloride | 483 | 0.72 | B |
| 314 | 1-(3-(4-(5H-Dibenzo[a,d]cyclohepten-5-ylidene)-1-piperidinyl)-1-propyl)-1-methoxycarbonylcyclohexane hydrochloride | 455 | 0.75 | B |
| 315 | 1-(3-Aminophenyl)-3-(4-(5H-dibenzo[a,d]cyclohepten-5-ylidene)-1-piperidinyl)propane dihydrochloride | 993 | 0.62 | B |
| 316 | 1-(3-Acetylaminophenyl)-3-(4-(5H-dibenzo[a,d]cyclohepten-5-ylidene)-1-piperidinyl)propane hydrochloride | 994 | 0.48 | B |
| 317 | 3-(4-(5H-Dibenzol[a,d]cyclohepten-5-ylidene)-1-piperidinyl)-1-(3,4,5-trimethoxyphenyl)propane dihydrochloride | 481 | 0.65 | B |
| 318 | 2-(3-(4-(5H-Dibenzo[a,d]cyclohepten-5-ylidene)-1-piperidinyl)-1-ethyl)-5,6-dimethoxy-1,2,3,4-tetrahydronaphthalene hydrochloride | 491 | 0.21 | H |
| 319 | 6-(4-(5H-Dibenzo[a,d]cyclohepten-5-ylidene)-1-piperidinyl)methyl-2,3-dimethoxybenzocycloheptene hydrochloride | 491 | 0.56 | H |
| 320 | 4-(5H-Dibenzo[a,d]cyclohepten-5-ylidene)-1-(3,4,5-trimethoxycinnamyl)piperidine hydrochloride | 479 | 0.69 | B |
| 321 | 1-(N-Acetyl-4-piperidinyl)-5-(4-(5H-Dibenzo[a,d]cyclohepten-5-ylidene)-1-piperidinyl)-1-pentene | 466 | 0.33 | B |

-continued

| exp | compound | MD (M+) | TLC (Rf) | solvent |
|---|---|---|---|---|
| | dihydrochloride | | | |
| 322 | 2-(4-(4-(5H-Dibenzo[a,d]cyclohepten-5-ylidene)-1-piperidinyl)-1-butyl)-3,4,5,6-tetramethyl-1,4-dihydropyridine-3,5-dicarboxylate hydrochloride | 1000 | 0.30 | B |
| 323 | 2-(4-(4-(5H-Dibenzo[a,d]cyclohepten-5-ylidene)-1-piperidinyl)-1-butyl)-3,4,5,6-tetramethylpyridine-3,5-dicarboxylate hydrochloride | 550 | 0.43 | B |
| 324 | 1-(1-(4-Methoxy)cyclohexyl)-3-(4-(5H-Dibenzo[a,d]cyclohepten-5-ylidene)-1-piperidinyl)propane hydrochloride | 427 | 0.48 | B |
| 325 | (5H-Dibenzo[b,e]thiepiz-5-ylidene)-1-(4-nitrocinnamyl)piperidine hydrochloride | 454 | 0.89 | B |
| 326 | 1-(4-Aminocinnamyl)-4-(5H-Dibenzo[b,e]thiepiz-5-ylidene)piperidine dihydrochloride | 424 | 0.65 | B |
| 327 | 1-(4-Acetylaminominocinnamyl)-4-(5H-Dibenzo[b,e]thiepiz-5-ylidene)piperidine hydrochloride | 466 | 0.58 | B |
| 328 | 3-(4-(5H-Dibenzo[a,d]cyclohepten-5-ylidene)-1-piperidinyl)-1-(2,4-dimethoxyphenyl)propane dihydrochloride | 451 | 0.64 | B |
| 329 | 2-(4-(5H-Dibenzo[a,d]cyclohepten-5-ylidene)-1-piperidinyl)methyl-4'-nitroindan hydrochloride | 448 | 0.49 | I |
| 330 | 4'-Amino-2-(4-(5H-Dibenzo[a,d]cyclohepten-5-ylidene)-1-piperidinyl)methylindan hydrochloride | 418 | 0.38 | H |
| 331 | 4'Acetylamino-2-(4-(5H-Dibenzo[a,d]cyclohepten-5-ylidene)-1-Piperidinyl)methylindan hydrochloride | 460 | 0.33 | B |
| 332 | 2-(4-(5H-Dibenzo[a,d]cyclohepten-5-ylidene)-1-piperidinyl)methyl-5'-nitroindan hydrochloride | 448 | 0.50 | I |
| 333 | 5'-Amino2-(4-(5H-Dibenzo[a,d]cyclohepten-5-ylidene)-1-piperidinyl)methylindan hydrochloride | 418 | 0.34 | B |
| 334 | 5'-Acetylamino-2-(4-(5H-Dibenzo[a,d]cyclohepten-5-ylidene)-1-piperidinyl)methyllindan hydrochloride | 460 | 0.29 | H |
| 335 | 4-Amino-N-(2-(5H-dibenzo[a,d]cyclohepten-5-ylidene)-1-piperidinyl)ethylbenzamide hydrochloride | 435 | | B |
| 336 | 3-Amino-N-(2-(5H-dibenzo[a,d]cyclohepten-5-ylidene)-1-piperidinyl)ethylbenzamide hydrochloride | 435 | | B |
| 337 | 1-Formyl-N-(2-(5H-Dibenzo[a,d]cyclohepten-5-ylidene)-1-piperidinyl)ethylisonicotinamide hydrochloride | 455 | | B |
| 338 | 1-Formyl-N-(2-(5H-dibenzo[a,d]cyclohepten-5-ylidene)-1-piperidinyl)ethylisonicotinamide hydrochloride | 455 | | B |
| 339 | N-(2-(5H-Dibenzo[a,d]cyclohepten-5-ylidene)-1-piperidinyl)ethynicotinamide hydrochloride | 421 | 0.42 | B |
| 340 | N-(2-(5H-Dibenzo[a,d]cyclohepten-5-ylidene)-1-piperidinyl)ethnicotinamide N-oxide hydrochloride | 437 (H+) | 0.27 | D |
| 341 | N-(2-(5H-Dibenzo[a,d]cyclohepten-5-ylidene)-1-piperidinyl)ethylisonicotinamide N-oxide hydrochloride | 437 (H+) | 0.30 | D |
| 342 | 4-(5H-Dibenzo[a,d]cyclohepten-5-ylidene)-1-(2,4-dimethoxycinnamyl)piperidine hydrochloride | 449 | 0.73 | B |
| 343 | 4-(5H-Dibenzo[a,d]cyclohepten-5-ylidene)-1-(2,5-dimethoxycinnamyl)piperidine hydrochloride | 449 | 0.73 | B |
| 344 | 4-(5H-Dibenzo[a,d]cyclohepten-5-ylidene)-1-(2,3-dimethoxycinnamyl)piperidine hydrochloride | 449 | 0.90 | B |
| 345 | 4-(5H-Dibenzo[a,d]cyclohepten-5-ylidene)-1-(3,5-dimethoxycinnamyl)piperidine hydrochloride | 449 | 0.74 | B |
| 346 | 1-(4-Cyanocinnamyl)-4-(5H-Dibenzo[a,d]cyclohepten-5-ylidene)piperidine hydrochloride | 414 | 0.70 | B |
| 347 | 4-(5H-Dibenzo[a,d]cyclohepten-5-ylidene)-1-(2-methoxycinnamyl)piperidine hydrochloride | 419 | 0.87 | B |
| 348 | 4-(5H-Dibenzo[a,d]cyclohepten-5-ylidene)-1-(3-methoxycinnamyl)piperidine hydrochloride | 419 | 0.89 | B |
| 349 | 4-(5H-Dibenzo[a,d]cyclohepten-5-ylidene)-1-(4-methoxycinnamyl)piperidine hydrochloride | 419 | 0.85 | B |
| 350 | 4-(10.11-Dihydro-5H-dibenzo[a,d]cyclohepten-5-ylidene)-1-(4-nitrocinnamyl)piperidine hydrochloride | 436 | 0.93 | B |
| 351 | 1-(4-Aminocinnamyl)-4-(10.11-dihydro-5H-Dibenzo[a,d]cyclohepten-5-ylidene)piperidine dihydrochloride | 406 | 0.64 | B |
| 352 | 1-(4-Acetylaminocinnamyl)-4-(10.11 dihydro-5H-Dibenzo[a,d]cyclohepten-5-ylidene)piperidine dihydrochloride | 448 | 0.54 | B |
| 353 | 4-(5H-Dibenzo[a,d]cyclohepten-5-ylidene)-1-(4-fluorocinnamyl)piperidine hydrochloride | 407 | 0.88 | B |
| 354 | 2-(2-(4-(5H-Dibenzo[a,d]cyclohepten-5-ylidene)-1-piperidinyl)-1-ethyl)-4'-nitroindan hydrochloride | 462 | 0.34 | H |
| 355 | 4'-Amino-2-(2-(4-(5H-Dibenzo[a,d]cyclohepten-5-ylidene)-1-pioperidinyl)-1-ethyl)indan hydrochloride | 432 | 0.53 | B |
| 356 | 4'-Acetylamino-2-(2-(4-(5H-Dibenzo[a,d]cyclohepten-5-ylidene)-1-piperidinyl)-1-ethyl)indan hydrochloride | 474 | 0.24 | B |
| 357 | 2-(2-(4-(5H-Dibenzo[a,d]cyclohepten-5-ylidene)-1-piperidinyl)-1-ethyl)-5'-nitroindan hydrochloride | 462 | 0.31 | H |
| 358 | 5'-Amino-2-(2-(4-(5H-Dibenzo[a,d]cyclohepten-5-ylidene)-1-piperidinyl)-1-ethyl)indan dihydrochloride | 432 | 0.23 | H |
| 359 | 5'-Acetylamino-2-(2-(4-(5H-Dibenzo[a,d]cyclohepten-5-ylidene)-1-piperidinyl)-1-ethyl)indan dihydrochloride | 474 | 0.05 | H |
| 360 | 2-(2-(4-(5H-Dibenzo[a,d]cyclohepten-5-ylidene)-1-piperidinyl)-1-ethyl)-5'-methanesulfonylaminoindan hydrochloride | 510 | 0.11 | H |
| 361 | 1-(Cyclohexyl-4-(4-(10.11-dihydroxy-5H-Dibenzo[a,d]cyclohepten-5-ylidene)-1-piperidinyl)butane | 445 | 0.84 | B |
| 362 | 3-(4-(5H-Dibenzo[a,d]cyclohepten-5-ylidene)-1-piperidinyl)-1-(3-pyridyl)-1-propene dihydrochloride | 390 | 0.44 | B |
| 363 | 4-(5H-Dibenzo[a,d]cyclohepten-5-ylidene)-1-(4-hydroxycinnamyl)piperdine hydrochloride | 406 (H+) | 0.55 | B |
| 364 | 1-(4-Acetoxycinnamyl)-4-(5H-Dibenzo[a,d]cyclohepten-5-ylidene)piperidine hydrochloride | 447 | 0.87 | B |
| 365 | 4-(5H-Dibenzo[a,d]cyclohepten-5-ylidene)-1-(4-hydroxy-3-methoxynamyl)piperidine hydrochloride | 435 | 0.63 | B |
| 366 | 1-(4-Acetoxy-3-methoxycinnamyl)-4-(5H-Dibenzo[a,d]cyclohepten-5-ylidene)piperidine hydrochloride | 477 | 0.83 | B |
| 367 | 4-(5H-Dibenzo[a,d]cyclohepten-5-ylidene)-1-(3-hydroxycinnamyl)piperidine hydrochloride | 405 | 0.45 | B |
| 368 | 1-(3-Acetoxycinnamyl)-4-(5H-Dibenzo[a,d]cyclohepten-5-ylidene)piperidine hydrochloride | 447 | 0.80 | B |
| 369 | 4-(5H-Dibenzo[a,d]cyclohepten-5-ylidene)-1-(3-(2-methoxyacetoxy)cinnamyl)piperidine hydrochloride | 477 | 0.65 | B |
| 370 | 4-(5H-Dibenzo[a,d]cyclohepten-5-ylidene)-1-(4-propanoylaminocinnamyl)piperidine hydrochloride | 460 | 0.21 | H |
| 371 | 4-(5H-Dibenzo[a,d]cyclohepten-5-ylidene)-1-(4-ethoxycarbonylaminocinnamyl)piperidine hydrochloride | 476 | 0.20 | H |
| 372 | 4-(5H-Dibenzo[a,d]cyclohepten-5-ylidene)-1-(4-methanesulfonylaminocinnamyl)piperidine hydrochloride | 482 | 0.44 | B |
| 373 | 1-(N,N-Bis(methanesulfonyl)aminocinnamyl)-4-(5H-Dibenzo[a,d]cyclohepten-5-ylidene)piperidine hydrochloride | 560 | 0.88 | B |
| 374 | 4-(5H-Dibenzo[a,d]cyclohepten-5-ylidene)-1-(2-methoxycarbonylcinnamyl)piperidine hydrochloride | 447 | 0.55 | B |
| 375 | 4-(5H-Dibenzo[a,d]cyclohepten-5-ylidene)-1-(3-methoxycarbonylcinnamyl)piperidine hydrochloride | 447 | 0.48 | H |
| 376 | 4-(5H-Dibenzo[a,d]cyclohepten-5-ylidene)-1-(4-methoxycarbonylcinnamyl)piperidine hydrochloride | 447 | 0.50 | B |
| 377 | 4-(5H-Dibenzo[a,d]cyclohepten-5-ylidene)-1-3-methoxy-2-nitrocinnamyl)piperidine hydrochloride | 464 | 0.30 | H |
| 378 | 4-(5H-Dibenzo[a,d]cyclohepten-5-ylidene)-1-(4-methoxycarbonylaminocinnamyl)piperidine hydrochloride | 462 | 0.53 | B |
| 379 | 4-(5H-Dibenzo[a,d]cyclohepten-5-ylidene)-1-(4-pivaloylaminocinnamyl)piperidine hydrochloride | 488 | 0.51 | B |
| 380 | 4-(5H-Dibenzo[a,d]cyclohepten-5-ylidene)-1-(4-trifluoroacetylaminocinnamyl)piperidine hydrochloride | 500 | 0.44 | B |
| 381 | 1-(4-Butanoylaminocinnamyl)-4-(5H-Dibenzo[a,d]cyclohepten-5-ylidene)piperidine hydrochloride | 474 | 0.50 | B |
| 382 | 4-(5H-Dibenzo[a,d]cyclohepten-5-ylidene)-1-(4-ethoxycarbonylcinnamyl)piperidine hydrochloride | 477 | 0.85 | B |
| 383 | 4-(5H-Dibenzo[a,d]cyclohepten-5-ylidene)-1-(4-(2-methoxyacetoxy)cinnamyl)piperidine hydrochloride | 477 | 0.45 | B |
| 384 | 4-(5H-Dibenzo[a,d]cyclohepten-5-ylidene)-1-(3,4-dihydroxycinnamyl)piperidine hydrochloride | 422 (H+) | 0.35 | B |
| 385 | 4-(5H-Dibenzo[a,d]cyclohepten-5-ylidene)-1-(2-indolylmethyl)piperidine hydrochloride | 402 | 0.67 | H |
| 386 | 1-(4-Aminosulfonylcinnamyl)-4-(5H-Dibenzo[a,d]cyclohepten-5-ylidene)piperidine hydrochloride | 468 (H+) | 0.48 | B |

-continued

| exp | compound | MD (M+) | TLC (Rf) | solvent |
|---|---|---|---|---|
| 387 | 4-(5H-Dibenzo[a,d]cyclohepten-5-ylidene)-1-(3-methoxy-4-nitrocinnamyl)piperidine hydrochloride | 464 | 0.29 | H | solvent: solvent for TLC
A: chloroform/methanol = 4/1
B: chloroform/methanol = 9/1
C: chloroform/methanol = 20/1
D: chloroform/methanol = 25/1
E: chloroform/methanol = 50/1
F: ethylacetate/hexane = 5/1
G: ethylacetate/hexane = 3/1
H: ethylacetate/hexane = 1/1
I: ethylacetate/hexane = 1/2
G: ethylacetate/hexane = 1/5

EXAMPLE 154

As test animals, four male spontaneously hypertensive rats (weight 400 to 440 g) that were sufficiently adapted for feeding and in which hypertension was confirmed were used.

Physiological saline aqueous solution containing 2.5% Nicolle and 2.5% ethanol of sample was intravenously administered by bolus injection at a dose of 1 ml per 1 kg of body weight. Systolic blood pressure after administration was measured by the indirect (tail-cuff) method.

The results are shown below.

| Compound | Dose (mg/kg) | Decrease in systolic blood pressure (mmHg) time after administration (hour) | |
|---|---|---|---|
| | | 0.5 | 4 |
| 1 | 10 | −67 | 1 |
| 2 | 10 | −125 | −34 |
| 3 | 3 | −110 | −22 |
| 4 | 10 | −76 | 0 |
| 5 | 10 | −56 | −20 |
| 7 | 10 | −57 | −15 |
| 8 | 10 | −95 | −21 |
| 9 | 10 | −91 | −19 |
| 10 | 10 | −129 | −21 |
| 11 | 10 | −166 | |
| 12 | 10 | −27 | 1 |
| 13 | 10 | −47 | 4 |
| 14 | 10 | −105 | −10 |
| 15 | 10 | −130 | −136 |
| 16 | 10 | −114 | −30 |
| 17 | 10 | −84 | −16 |
| 20 | 10 | −37 | 2 |
| 23 | 10 | −34 | 10 |
| 25 | 10 | −8 | −7 |
| 28 | 10 | −52 | 4 |
| 31 | 10 | −61 | −11 |
| 37 | 10 | −78 | −36 |
| 38 | 10 | −140 | −76 |
| 42 | 10 | −66 | −14 |
| 45 | 10 | −147 | −38 |
| 52 | 10 | −23 | −9 |
| 59 | 10 | −87 | −21 |
| 60 | 10 | −121 | −48 |
| 100 | 10 | −35 | −5 |
| 101 | 10 | −89 | −14 |
| 107 | 10 | −88 | −11 |
| 108 | 10 | −126 | −50 |
| 111 | 10 | −98 | −13 |
| 112 | 10 | −16 | 0 |
| 113 | 1 | −151 | −81 |
| 115 | 10 | −53 | −19 |
| 116 | 10 | −36 | −12 |
| 117 | 10 | −143 | −25 |
| 118 | 10 | −129 | −24 |
| 119 | 10 | −34 | −5 |
| 120 | 3 | −17 | −12 |
| 121 | 10 | −42 | −19 |
| 122 | 10 | −120 | −62 |
| 123 | 10 | −55 | −7 |
| 124 | 10 | −90 | −20 |
| 125 | 10 | −93 | −14 |
| 126 | 10 | −87 | −19 |
| 128 | 10 | −129 | −8 |
| 129 | 10 | −17 | −1 |
| 130 | 10 | −42 | 9 |
| 131 | 10 | −116 | 2 |
| 132 | 10 | −106 | −5 |
| 133 | 3 | −146 | −84 |
| 134 | 10 | −115 | −30 |
| 135 | 10 | −132 | −50 |
| 136 | 10 | −100 | −40 |
| 138 | 10 | −129 | −33 |
| 139 | 10 | −139 | −89 |
| 140 | 3 | −113 | −101 |
| 142 | 10 | −43 | 0 |
| 149 | 10 | −116 | −32 |
| 150 | 10 | −110 | −47 |
| 151 | 10 | −81 | −43 |
| 154 | 10 | −131 | −105 |
| 155 | 10 | −131 | −105 |
| 156 | 10 | −110 | −42 |
| 157 | 10 | −32 | −13 |
| 158 | 10 | −8 | 7 |
| 159 | 10 | −27 | −12 |
| 160 | 10 | −3 | −10 |
| 161 | 10 | −64 | −12 |
| 162 | 10 | −62 | −3 |
| 163 | 10 | −1 | 4 |
| 164 | 10 | −91 | −22 |
| 165 | 10 | −22 | 12 |
| 166 | 10 | −45 | 6 |
| 168 | 10 | −108 | 0 |
| 169 | 10 | −130 | −4 |
| 171 | 10 | −122 | −8 |
| 172 | 10 | −115 | −25 |
| 173 | 10 | −98 | −25 |
| 174 | 10 | −8 | −16 |
| 175 | 10 | −87 | −1 |
| 176 | 10 | −105 | −10 |
| 180 | 10 | −25 | −24 |
| 181 | 10 | −56 | −27 |
| 182 | 10 | −11 | −6 |
| 184 | 10 | −16 | −4 |
| 185 | 10 | −66 | −10 |
| 186 | 10 | −95 | −12 |
| 187 | 10 | −47 | −9 |
| 188 | 10 | −94 | −12 |
| 189 | 10 | −72 | −15 |
| 190 | 10 | −11 | −15 |
| 191 | 10 | −29 | −20 |
| 192 | 10 | −25 | −36 |
| 193 | 10 | −124 | −59 |
| 194 | 10 | −59 | −17 |
| 195 | 10 | −100 | −51 |
| 196 | 10 | −145 | −81 |
| 197 | 10 | −51 | −26 |
| 198 | 10 | −124 | −25 |
| 199 | 10 | −15 | −24 |
| 200 | 10 | −10 | −24 |
| 201 | 10 | −118 | −21 |
| 202 | 10 | −54 | −16 |

-continued

| Compound | Dose (mg/kg) | Decrease in systolic blood pressure (mmHg) time after administration (hour) | |
|---|---|---|---|
| | | 0.5 | 4 |
| 203 | 3 | −123 | −58 |
| 204 | 10 | −141 | −84 |
| 205 | 10 | −22 | −4 |
| 206 | 10 | −61 | −27 |
| 207 | 10 | −98 | −43 |
| 208 | 10 | −131 | −19 |
| 209 | 10 | −49 | −13 |
| 210 | 1 | −78 | −69 |
| 212 | 10 | −155 | |
| 213 | 10 | −82 | 3 |
| 214 | 10 | −126 | −21 |
| 215 | 10 | −128 | −14 |
| 216 | 3 | −2 | −27 |
| 217 | 10 | −18 | −20 |
| 218 | 10 | −97 | −11 |
| 219 | 10 | −104 | −33 |
| 220 | 10 | −148 | −54 |
| 221 | 10 | −70 | −13 |
| 222 | 10 | −94 | −5 |
| 224 | 10 | −69 | −61 |
| 225 | 10 | −115 | −31 |
| 226 | 10 | −131 | −16 |
| 228 | 3 | −112 | −14 |
| 229 | 3 | −77 | −14 |
| 230 | 3 | −131 | −91 |
| 231 | 3 | −132 | −115 |
| 232 | 1 | −92 | −85 |
| 233 | 10 | −35 | −1 |
| 234 | 10 | −96 | −2 |
| 235 | 10 | −99 | −5 |
| 236 | 10 | −10 | −15 |
| 237 | 10 | −65 | −14 |
| 238 | 10 | −14 | −5 |
| 239 | 10 | −68 | −15 |
| 240 | 3 | −118 | −5 |
| 241 | 10 | −73 | −4 |
| 242 | 10 | −28 | 7 |
| 243 | 10 | −111 | −31 |
| 244 | 10 | −19 | 4 |
| 245 | 10 | −34 | −10 |
| 246 | 10 | −34 | −4 |
| 247 | 10 | −119 | −40 |
| 248 | 10 | −101 | −92 |
| 249 | 10 | −121 | −100 |
| 250 | 10 | −136 | −30 |
| 251 | 10 | −110 | −24 |
| 252 | 10 | −23 | −5 |
| 253 | 10 | −12 | 1 |
| 255 | 10 | −62 | 2 |
| 256 | 10 | −60 | −11 |
| 257 | 10 | −70 | −13 |
| 258 | 10 | −74 | −10 |
| 259 | 10 | −46 | −5 |
| 260 | 10 | −51 | −10 |
| 261 | 10 | −123 | −11 |
| 262 | 10 | −16 | −3 |
| 264 | 10 | −38 | −5 |
| 265 | 10 | −61 | −11 |
| 266 | 10 | −133 | −77 |
| 267 | 10 | −40 | 0 |
| 268 | 10 | −29 | 13 |
| 269 | 10 | 143 | −71 |
| 270 | 10 | −18 | 2 |
| 271 | 10 | −17 | −13 |
| 272 | 10 | −76 | −3 |
| 273 | 10 | −37 | 5 |
| 274 | 10 | −102 | −21 |
| 275 | 10 | −66 | −20 |
| 276 | 10 | −24 | −1 |
| 277 | 10 | −27 | 0 |
| 278 | 10 | −64 | 2 |
| 279 | 3 | −83 | −24 |
| 280 | 10 | −50 | −11 |
| 281 | 10 | −31 | −5 |
| 282 | 10 | −72 | −15 |
| 283 | 10 | −112 | 4 |
| 284 | 3 | −151 | −40 |
| 285 | 10 | −62 | −7 |

-continued

| Compound | Dose (mg/kg) | Decrease in systolic blood pressure (mmHg) time after administration (hour) | |
|---|---|---|---|
| | | 0.5 | 4 |
| 286 | 10 | −134 | −40 |
| 287 | 10 | −83 | −16 |
| 288 | 10 | −92 | −14 |
| 289 | 3 | −20 | 10 |
| 290 | 3 | −15 | 15 |
| 291 | 3 | −8 | 15 |
| 292 | 3 | −31 | 3 |
| 293 | 10 | −122 | 4 |
| 294 | 3 | −17 | 7 |
| 295 | 3 | −36 | 1 |
| 296 | 10 | −109 | −14 |
| 297 | 10 | −129 | −57 |
| 298 | 10 | −111 | −31 |
| 299 | 10 | −134 | −45 |
| 300 | 10 | −97 | −22 |
| 301 | 10 | −100 | −12 |
| 302 | 10 | −83 | −41 |
| 303 | 3 | −90 | −19 |
| 304 | 10 | −49 | −5 |
| 305 | 10 | −95 | −9 |
| 306 | 10 | −138 | −37 |
| 307 | 10 | −62 | −20 |
| 308 | 3 | −27 | −5 |
| 310 | 10 | −90 | −18 |
| 311 | 10 | −90 | −18 |
| 312 | 10 | −115 | −11 |
| 313 | 10 | −154 | −85 |
| 314 | 10 | −61 | −11 |
| 315 | 10 | −43 | −3 |
| 316 | 1 | −100 | 8 |
| 317 | 10 | −118 | −14 |
| 318 | 10 | −83 | −57 |
| 319 | 10 | −104 | −20 |
| 320 | 10 | −147 | −113 |
| 321 | 10 | −60 | −4 |
| 322 | 10 | −100 | −16 |
| 323 | 10 | −117 | −11 |
| 324 | 10 | −137 | −46 |
| 325 | 10 | −115 | −100 |
| 326 | 1 | −125 | −102 |
| 327 | 3 | −10 | −43 |
| 328 | 10 | −125 | −87 |
| 329 | 10 | −34 | −7 |
| 330 | 10 | −93 | −25 |
| 331 | 10 | −62 | −14 |
| 332 | 10 | −111 | −57 |
| 343 | 3 | −83 | −45 |
| 344 | 1 | −123 | −35 |
| 345 | 3 | −120 | −95 |
| 346 | 3 | −142 | −121 |
| 347 | 3 | −116 | −53 |
| 348 | 3 | −105 | −12 |
| 349 | 1 | −48 | −43 |
| 350 | 10 | −136 | −85 |
| 351 | 3 | −70 | −21 |
| 352 | 3 | −93 | −60 |
| 353 | 10 | −147 | −138 |
| 354 | 3 | −89 | −8 |
| 363 | 3 | −120 | |
| 364 | 1 | −113 | |
| 365 | 3 | −80 | −56 |
| 366 | 3 | −152 | −113 |
| 367 | 10 | −98 | −63 |
| 368 | 3 | −110 | −68 |
| 369 | 10 | −101 | −83 |
| 370 | 10 | −99 | −69 |
| 374 | 3 | −119 | 11 |
| 375 | 1 | −126 | −70 |
| 376 | 3 | −106 | −77 |
| 377 | 1 | −151 | −73 |
| 378 | 1 | −106 | −90 |
| 379 | 1 | −118 | −59 |
| 380 | 0.3 | −141 | |
| 381 | 3 | −136 | |
| 382 | 3 | −129 | −74 |
| 383 | 3 | −112 | −86 |
| 384 | 3 | −130 | −93 |
| 385 | 10 | −123 | −96 |

-continued

| Compound | Dose (mg/kg) | Decrease in systolic blood pressure (mmHg) time after administration (hour) | |
|---|---|---|---|
| | | 0.5 | 4 |
| 386 | 10 | −83 | −96 |
| 387 | 10 | −112 | −50 |

EFFECTS OF THE INVENTION

From the foregoing results, it is understood that the piperidine derivatives of the present invention possess hypotensive activity and are usable as hypotensives and therefore, they can be expected to provide an excellent hypotensive effect. Accordingly, the present invention is extremely useful, particularly in the pharmaceutical industry.

Having now fully described the invention, it will be apparent to one of ordinary skill in the art that many changes and modifications can be made thereto without departing from the spirit or scope of the invention as set forth herein.

What is claimed as new and is intended to be secured by Letters Patent of the United States is:

1. A piperidine compound of the formula (I)

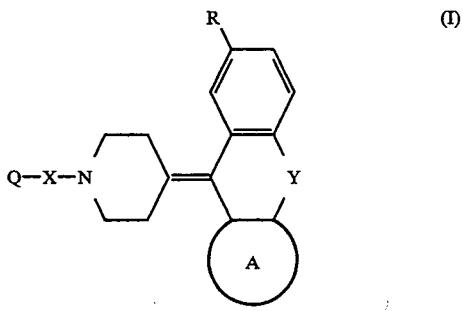

wherein:
A is pyridine;
R is —H, —Cl or —OCH$_3$;
X is —(CH$_2$)$_n$—, —CO—(CH$_2$)$_3$, —CONH—(CH$_2$)$_2$, —NHCO—(CH$_2$)$_2$, or —CH=CH—(CH$_2$)$_2$—; and
n is an integer of from 3 to 5;
Y is —CH=CH—, —(CH$_2$)$_2$, —OCH$_2$—, —SCH$_2$—, or —O—; and
Q is —CN, substituted or unsubstituted cyclohexyl, substituted or unsubstituted piperidinyl, substituted or unsubstituted piperazinyl, substituted or unsubstituted phenyl, substituted or unsubstituted furyl, substituted or unsubstituted thienyl, substituted or unsubstituted pyrrolyl, substituted or unsubstituted pyridyl, substituted or unsubstituted morpholinyl, or substituted or unsubstituted thiomorpholinyl, wherein when Q is substituted, the substituent(s) is/are selected from the group consisting of H-(CH$_2$)$_n$- wherein n is an integer of 1 to 10, Cl-(CH$_2$)$_5$, allyl, formyl, phenyl, isopropyl, hydroxy, methoxy, ethoxy, fluoro, chloro, acetoxy, 2-methoxyacetoxy, ethoxycarboxyl, carboxyl, methoxycarbonyl, ethoxycarbonyl, cyano, imidazolylmethyl, trifluoromethyl, benzoyl, 2-hydroxybenzyl, nitro, amino, acetylamino, propanoylamino, butanoylamino, pivaloylamino, trifluoromethylamino, methoxycarbonylamino, ethoxycarbonylamino, cinnamoylamino, methanesulfonylamino, N,N-bis(methanesulfonyl)amino, aminocarbonyl, aminosulfonyl, hydroxymethyl and acetoxymethyl, and wherein when X and/or Q contain -(CH$_2$)- groups, one or more of the -(CH$_2$)- groups in X and/or Q may be substituted by -(CH$_2$)$_4$ or -(CH$_2$)$_5$, thereby forming a ring structure.

2. The piperidine compound of claim 1, wherein the hydrogen atoms of one or more of the —CH$_2$— groups in X and Q are substituted by -(CH$_2$)$_4$ or -(CH$_2$)$_5$, thereby forming a ring structure.

3. The piperidine compound of claim 1, wherein Q is substituted by at least one substituent selected from the group consisting of H-(CH$_2$)$_n$- wherein n is an integer of 1 to 10, Cl-(CH$_2$)$_5$, allyl, formyl, phenyl, isopropyl, hydroxy, methoxy, ethoxy, fluoro, chloro, acetoxy, 2-methoxyacetoxy, ethoxycarboxyl, carboxyl, methoxycarbonyl, ethoxycarbonyl, cyano, imidazolylmethyl, trifluoromethyl, benzoyl, 2-hydroxybenzyl, nitro, amino, acetylamino, propanoylamino, butanoylamino, pivaloylamino, trifluoromethylamino, methoxycarbonylamino, ethoxycarbonylamino, cinnamoylamino, methanesulfonylamino, N,N-bis(methanesulfonyl)amino, aminocarbonyl, aminosulfonyl, hydroxymethyl and acetoxymethyl.

4. The piperidine compound of claim 1, wherein X is —CONH—(CH$_2$)$_2$.

5. The piperidine compound of claim 1, wherein Y is —CH=CH—.

6. The piperidine compound of claim 1, wherein Y is —(CH$_2$)$_2$—.

7. The piperidine compound of claim 1, wherein Q is substituted or unsubstituted piperidinyl.

8. The piperidine compound of claim 1, wherein X is —CONH—(CH$_2$)$_2$, and Q is substituted or unsubstituted piperidinyl.

9. A piperidine compound of the formula

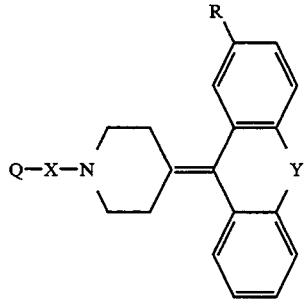

wherein:
R is —H, —Cl or —OCH$_3$;
X is —(CH$_2$)$_n$—, —CO—(CH$_2$)$_4$, —CONH—(CH$_2$)$_2$, —NHCO—(CH$_2$)$_2$, or —CH=CH—(CH$_2$)$_2$—; and
n is an integer of from 3 to 5;
Y is —CH=CH—, —(CH$_2$)$_2$—, —OCH$_2$—, —SCH$_2$—; and
Q is —CN, substituted or unsubstituted piperidinyl, substituted or unsubstituted piperazinyl, substituted or unsubstituted thienyl, substituted or unsubstituted morpholinyl, or substituted or unsubstituted thiomorpholinyl, wherein when Q is substituted, the substituent(s) is/are selected from the group consisting of H-(CH$_2$)$_3$ wherein n is an integer of 1 to 10, CL-(CH$_2$)$_3$, allyl, formyl, phenyl, isopropyl, hydroxy, methoxy, ethoxy, fluoro, chloro, acetoxy, 2-methoxyacetoxy, carboxyl, methoxycarbonyl, ethoxycarbonyl, cyano, imidazolylmethyl, trifluoromethyl, benzoyl, 2-hdyroxybenzyl, nitro, amino, acetylamino, propanoylamino, butanoylamino, pivaloylamino, trifluoromethylamino, methoxycarbonylamino, ethoxycarbonylamino, cinnamoylamino, methanesulfonylamino, N,N-bis(methanesulfonyl)amino, aminocarbonyl, aminosulfonyl, hydroxymethyl and acetoxymethyl, and wherein when X and/or Q contain $-(CH_2)-$ groups, one or more of the $-(CH_2)-$ groups in X and/or Q may be substituted by $-(CH_2)_4-$ or $-(CH_2)_5-$, thereby forming a ring structure.

10. The piperidine compound of claim 9, wherein X is —CONH—$(CH_2)_2$, Y is —CH=CH—, and Q is N-formylpiperidinyl.

11. A piperidine compound of the formula

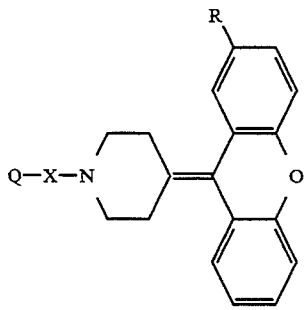

wherein:
R is —H, —Cl or —OCH$_3$;
X is —CO—$(CH_2)_3$, —CONH—$(CH_2)_2$, —NHCO—$(CH_2)_2$, or —CH=CH— $(CH_2)_2$—; and
Q is —CN, substituted or unsubstituted cyclohexyl, substituted or unsubstituted piperidinyl, substituted or unsubstituted piperazinyl, substituted or unsubstituted phenyl, substituted or unsubstituted furyl, substituted or unsubstituted thienyl, substituted or unsubstituted pyrrolyl, substituted or unsubstituted pyridyl, substituted or unsubstituted morpholinyl, or substituted or unsubstituted thiomorpholinyl, wherein when Q is substituted, the substituent(s) is/are selected from the group consisting of H$-(CH_2)_n-$ wherein n is an integer of 1 to 10, Cl$-(CH_2)_3-$, allyl, phenyl, isopropyl, hydroxy, methoxy, ethoxy, fluoro, chloro, acetoxy, 2-methoxyacetoxy, ethoxycarboxyl, carboxyl, methoxycarbonyl, ethoxycarbonyl, cyano, imidazolylmethyl, trifluoromethyl, benzoyl, 2-hydroxybenzyl, nitro, amino, acetylamino, propanoylamino, butanoylamino, pivaloylamino, trifluoromethylamino, methoxycarbonylamino, ethoxycarbonylamino, cinnamoylamino, methanesulfonylamino, N,N-bis(methanesulfonyl)amino, aminocarbonyl, aminosulfonyl, hydroxymethyl and acetoxymethyl, and wherein when X and/or Q contain $-(CH_2)-$ groups, one or more of the $-(CH_2)-$ groups in X and/or Q may be substituted by $-(CH_2)_4-$ or $-(CH_2)_5-$ thereby forming a ring structure.

12. A piperidine compound of the formula

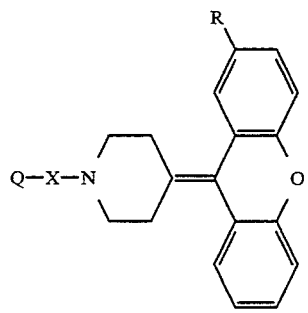

wherein:
R is —H, —Cl or —OCH$_3$;
X is —$(CH_2)_n$—;
n is an integer of from 3 to 5; and
Q is —CN, substituted or unsubstituted phenyl, substituted or unsubstituted furyl, substituted or unsubstituted thienyl, substituted or unsubstituted pyrrolyl, substituted or unsubstituted pyridyl, wherein when Q is substituted, the substituent(s) is/are selected from the group consisting of H$-(CH_2)_n-$ wherein n is an integer of 1 to 10, Cl$-(CH_2)_3-$, allyl, phenyl, isopropyl, hydroxy, methoxy, ethoxy, fluoro, chloro, acetoxy, 2-methoxyacetoxy, ethoxycarboxyl, carboxyl, methoxycarbonyl, ethoxycarbonyl, cyano, imidazolylmethyl, trifluoromethyl, benzoyl, 2-hydroxybenzyl, nitro, amino, acetylamino, propanoylamino, butanoylamino, pivaloylamino, trifluoromethylamino, methoxycarbonylamino, ethoxycarbonylamino, cinnamoylamino, methanesulfonylamino, N,N-bis(methanesulfonyl)amino, aminocarbonyl, aminosulfonyl, hydroxymethyl and acetoxymethyl, and wherein one or more of the $-(CH_2)-$ groups in X may be substituted by $-(CH_2)_4-$ or $-(CH_2)_5-$ thereby forming a ring structure.

* * * * *

UNITED STATES PATENT AND TRADEMARK OFFICE
CERTIFICATE OF CORRECTION

PATENT NO. : 5,393,890
DATED : February 28, 1995
INVENTOR(S) : Masataka Syoji et al It is certified that error appears in the above-identified patent and that said Letters Patent is hereby corrected as shown below:

Column 31, line 59, claim 1, delete "formyl".

Column 32, line 14, claim 3, delete "formyl".

Column 32, line 54, claim 9, in the formula, "4" should read --3--.

Column 32, line 66, claim 9, in the formula "3" should read --n--.

Column 32, line 67, claim 9, in the formula "CL" should read --Cl--.

Signed and Sealed this

Third Day of October, 1995

*Attest:*

BRUCE LEHMAN

*Attesting Officer*    *Commissioner of Patents and Trademarks*